(12) United States Patent
Schober et al.

(10) Patent No.: US 10,533,929 B2
(45) Date of Patent: Jan. 14, 2020

(54) METHOD OF USING MULTIPLE ROW SENSING DEVICE FOR A TIRE

(71) Applicants: Compagnie Generale des Etablissements Michelin, Clermont-Ferrand (FR); Michelin Recherche et Technique S.A., Granges-Paccot (CH); Bradley D. Schober, Greer, SC (US); Frank E. Gramling, Simpsonville, SC (US); David A. Judd, Mauldin, SC (US)

(72) Inventors: Bradley D. Schober, Greer, SC (US); Frank E. Gramling, Simpsonville, SC (US); David A. Judd, Mauldin, SC (US)

(73) Assignee: Compagnie Generale des Etablissements Michelin, Clermont-Ferrand (FR)

( * ) Notice: Subject to any disclaimer, the term of this patent is extended or adjusted under 35 U.S.C. 154(b) by 44 days.

(21) Appl. No.: 15/527,054

(22) PCT Filed: Jan. 5, 2016

(86) PCT No.: PCT/US2016/012119
§ 371 (c)(1),
(2) Date: May 16, 2017

(87) PCT Pub. No.: WO2016/111967
PCT Pub. Date: Jul. 14, 2016

(65) Prior Publication Data
US 2017/0370806 A1 Dec. 28, 2017

Related U.S. Application Data

(63) Continuation of application No. PCT/US2015/010159, filed on Jan. 5, 2015.

(51) Int. Cl.
G01M 17/02 (2006.01)
G01N 27/82 (2006.01)
G01N 27/83 (2006.01)

(52) U.S. Cl.
CPC ............ *G01M 17/02* (2013.01); *G01N 27/82* (2013.01); *G01N 27/83* (2013.01)

(58) Field of Classification Search
None
See application file for complete search history.

(56) References Cited

U.S. PATENT DOCUMENTS 3,967,498 A 7/1976 Pezzillo
4,475,384 A 10/1984 Christie
(Continued)

FOREIGN PATENT DOCUMENTS

EP 1037753 B1 9/2000
EP 1245948 A1 10/2002
(Continued)

OTHER PUBLICATIONS

International Search Report dated Apr. 29, 2015 for PCT/US2015/010154.
(Continued)

*Primary Examiner* — Peter J Macchiarolo
*Assistant Examiner* — Jermaine L Jenkins
(74) *Attorney, Agent, or Firm* — Dority & Manning, P.A.

(57) ABSTRACT

A method of using a sensor device for tire inspection is provided. Signals are received from multiples rows of sensors separated by a predetermined distance. The sensors are positioned next to the inner surface of the tire for inspection. Signals from the different rows of sensors are used to identify e.g., breaks in the reinforcements of the tire and also used to identify undesirable signals generated from vibration or jarring of the sensor device.

15 Claims, 18 Drawing Sheets

(56) References Cited

U.S. PATENT DOCUMENTS

| | | | |
|---|---|---|---|
| 4,520,307 A | 5/1985 | Weiss | |
| 5,557,256 A | 9/1996 | Achterholt | |
| 6,304,090 B1 * | 10/2001 | Weiss | G01M 17/02 324/516 |
| 6,832,513 B2 * | 12/2004 | Weiss | G01M 17/02 73/146 |
| 6,907,777 B2 * | 6/2005 | Weiss | G01M 17/02 73/146 |
| 7,826,192 B2 * | 11/2010 | Sinnett | G01M 17/022 156/123 |
| 9,927,326 B2 * | 3/2018 | Schober | B29D 30/0061 |
| 9,976,937 B2 * | 5/2018 | Charlat | G01M 17/027 |
| 10,006,835 B2 * | 6/2018 | Schober | G01R 33/072 |
| 10,060,832 B2 * | 8/2018 | Schober | G01M 17/02 |
| 2004/0016293 A1 | 1/2004 | Weiss | |
| 2006/0028203 A1 | 2/2006 | Kawashima | |
| 2006/0170420 A1 | 8/2006 | Nishimizu | |
| 2007/0028679 A1 | 2/2007 | Stoila et al. | |
| 2008/0168833 A1 | 7/2008 | Awad | |
| 2008/0300801 A1 | 12/2008 | Miyoshi | |
| 2009/0009162 A1 * | 1/2009 | Nishimizu | G01N 27/9033 324/238 |
| 2010/0276044 A1 | 11/2010 | Heise et al. | |
| 2012/0038357 A1 | 2/2012 | Brandon | |
| 2012/0112898 A1 | 5/2012 | Yu et al. | |
| 2012/0137761 A1 | 6/2012 | Dardelin | |
| 2013/0131915 A1 | 5/2013 | Masago | |
| 2013/0162265 A1 | 6/2013 | Beccavin et al. | |
| 2014/0070935 A1 | 3/2014 | Wang | |
| 2017/0227496 A1 * | 8/2017 | Judd | G01N 27/82 |

FOREIGN PATENT DOCUMENTS

| | | |
|---|---|---|
| EP | 1349249 A1 | 10/2003 |
| WO | WO2012/036674 A1 | 3/2012 |
| WO | WO2014/077846 | 5/2014 |

OTHER PUBLICATIONS

International Search Report dated Apr. 28, 2015 for PCT/US2015/010159.

International Search Report dated Mar. 31, 2016 for PCT/US2016/012116.

International Search Report dated Jul. 31, 2015 for PCT/US15/28211.

International Search Report dated Aug. 11, 2016 for PCT/US2016/23924.

International Search Report dated Mar. 23, 2016 for PCT/US2016/012119.

* cited by examiner

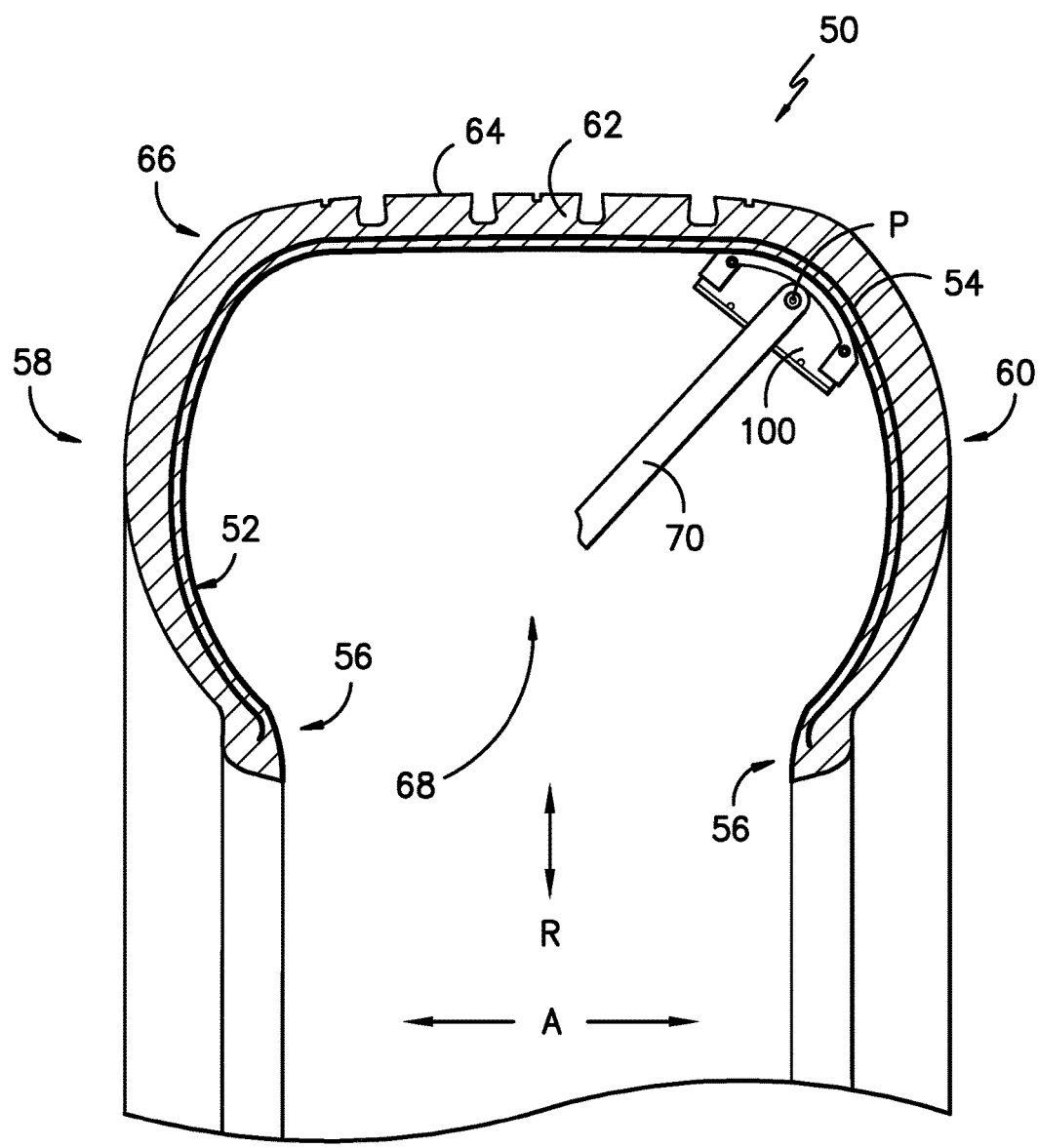
FIG. —1—

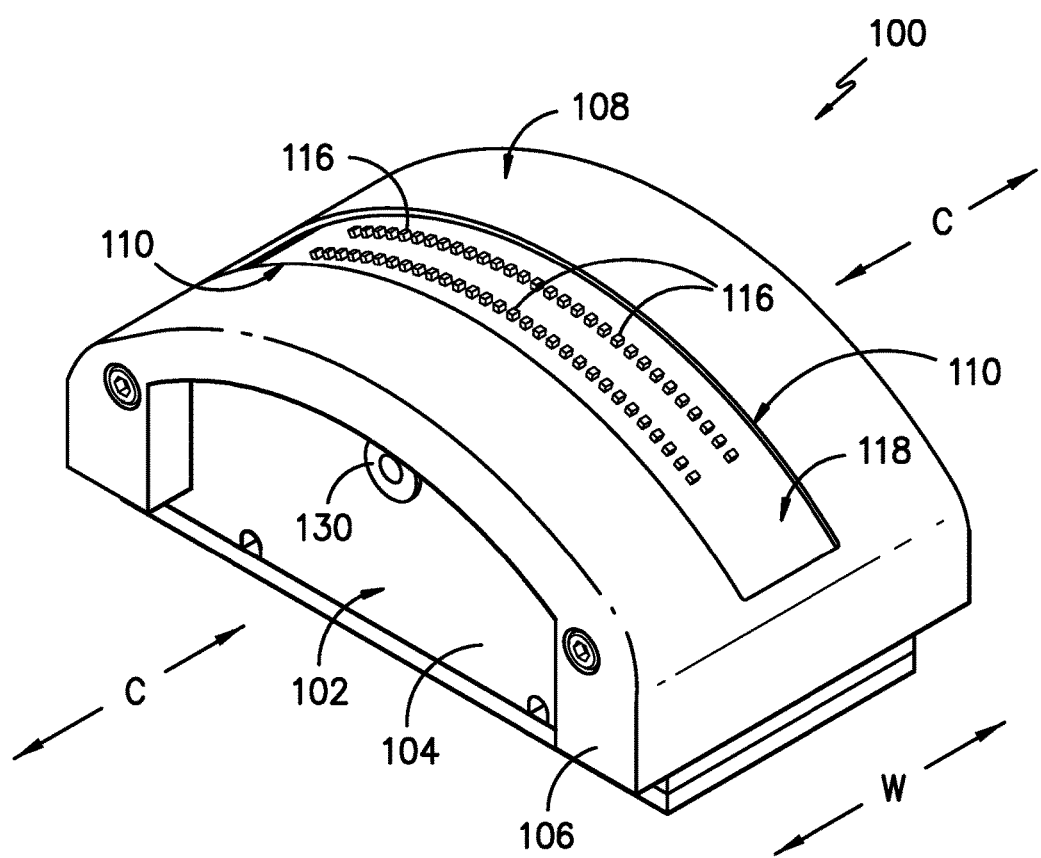
FIG. -2-

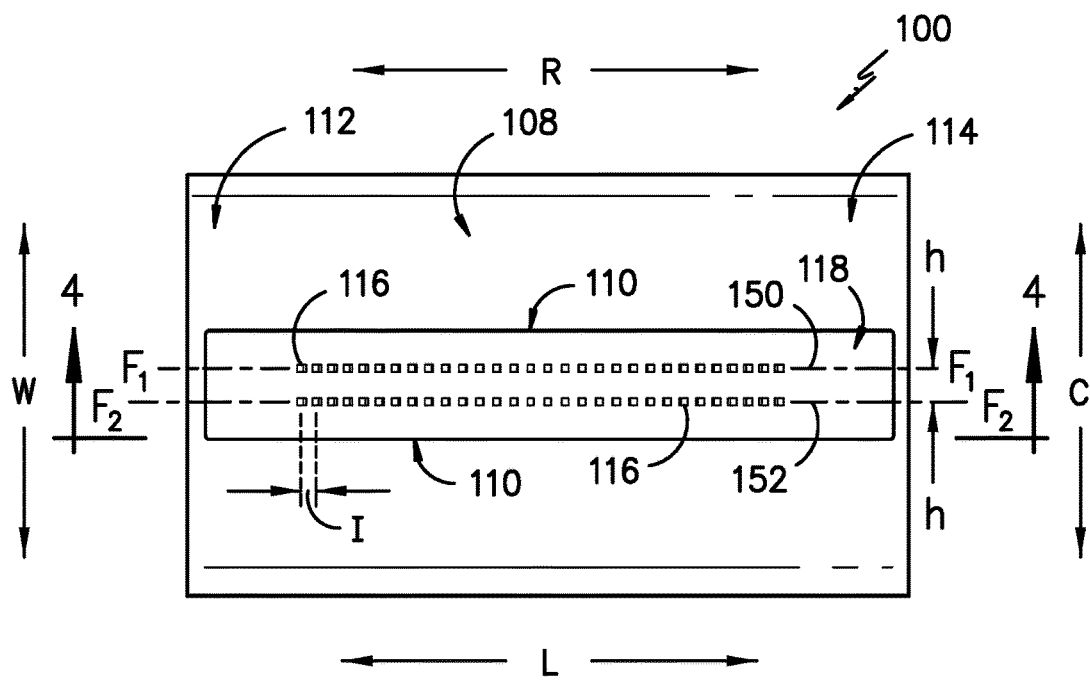
FIG. -3-
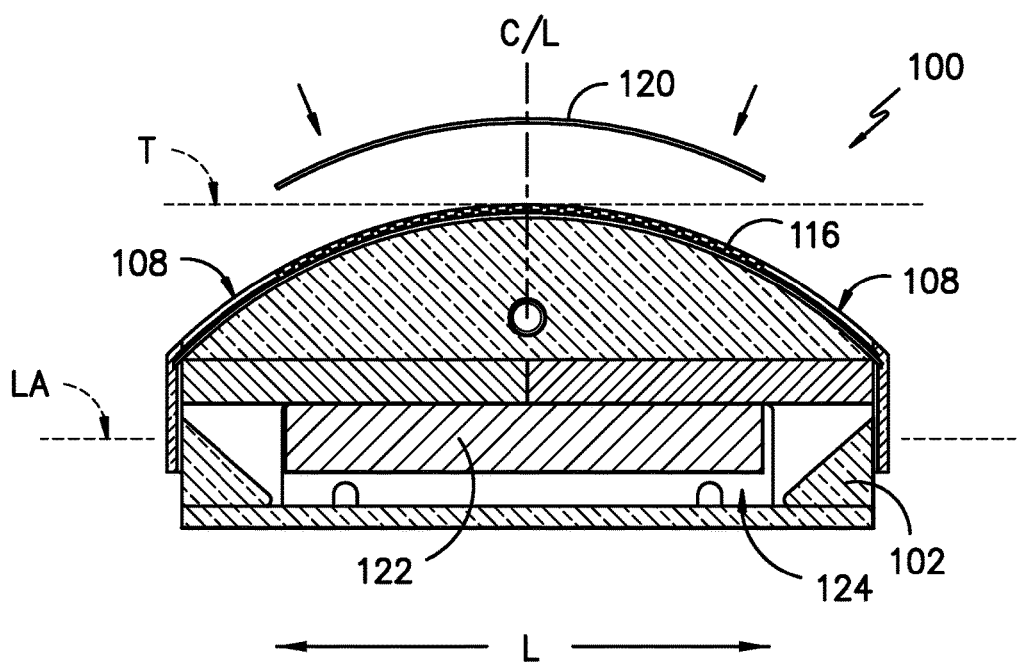
FIG. -4-

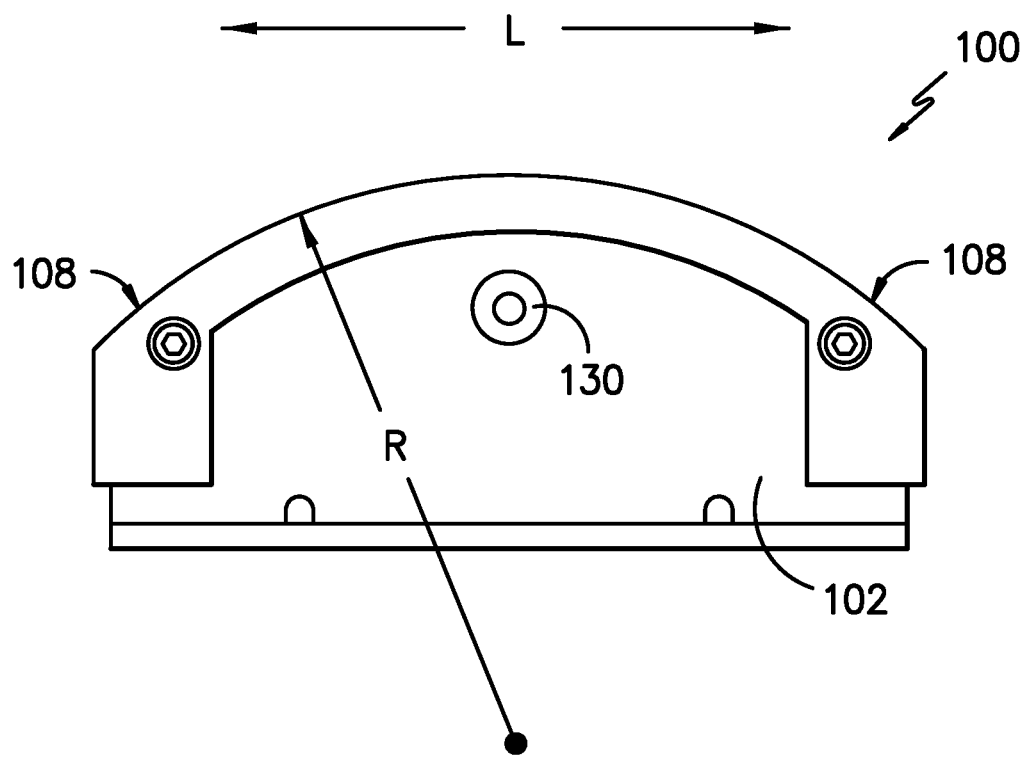
FIG. -5-

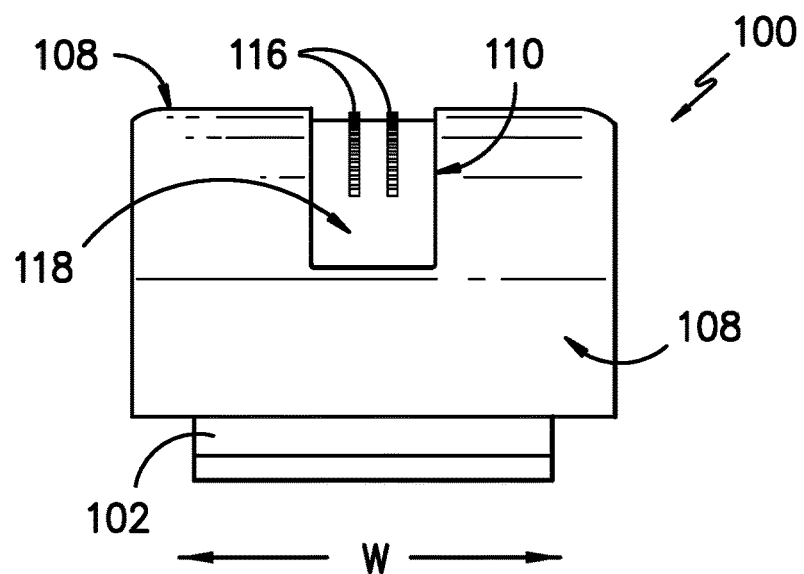
FIG. -6-
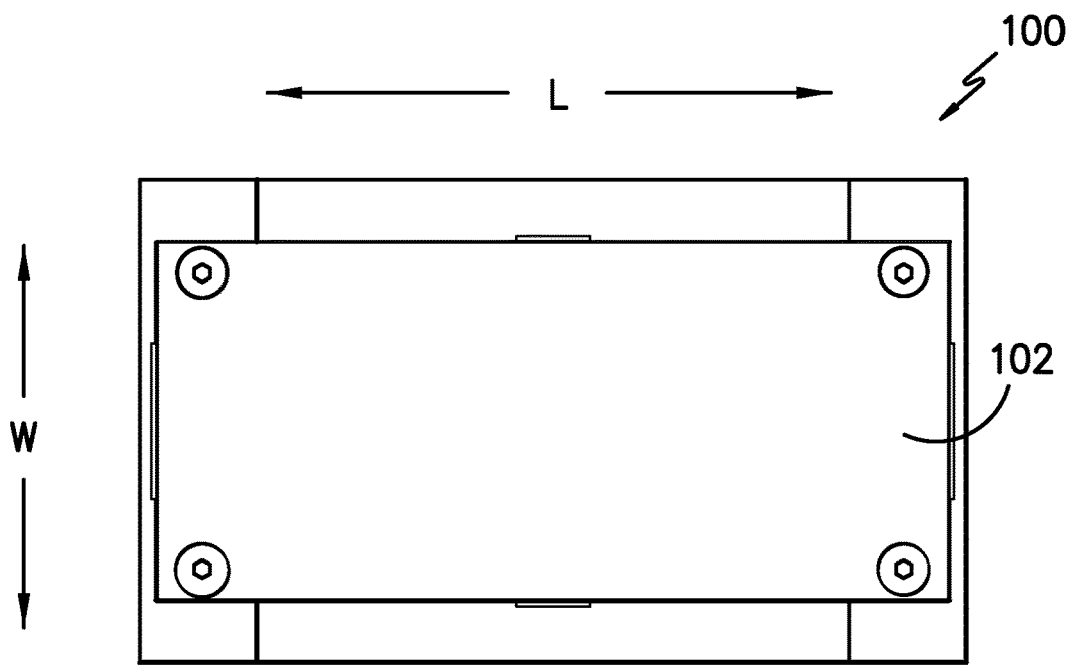
FIG. -7-

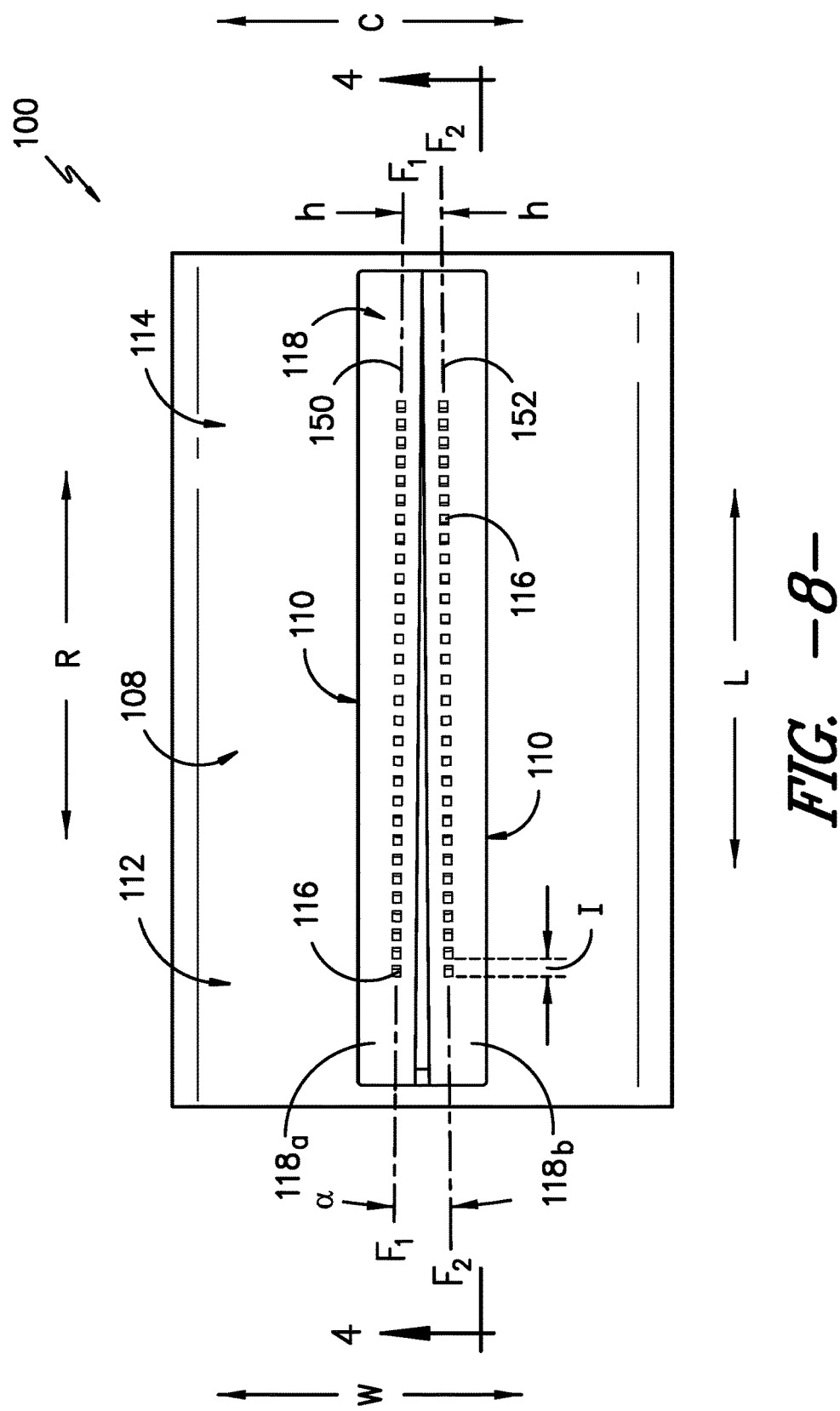
FIG. -8-

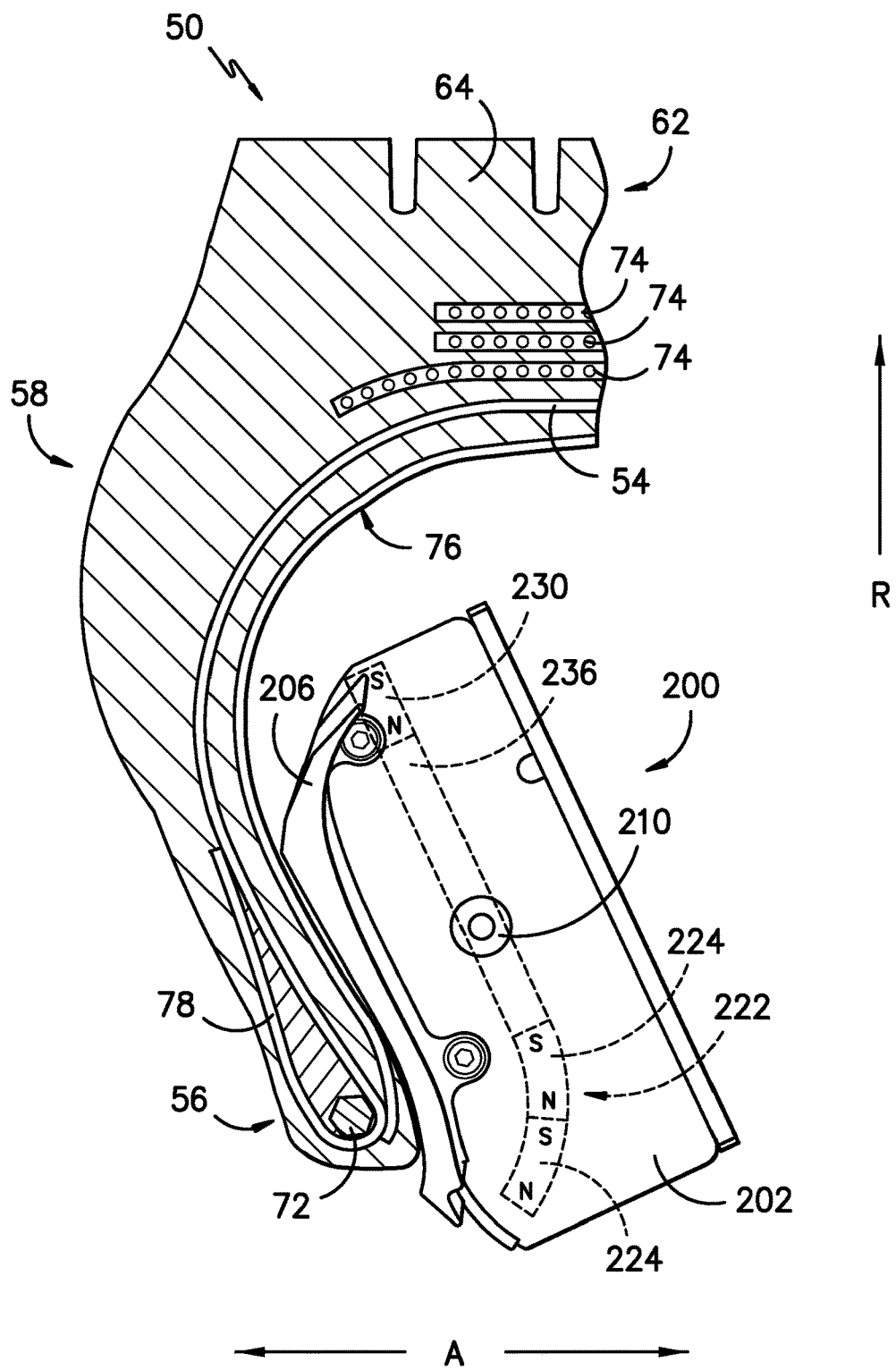
FIG. -9-

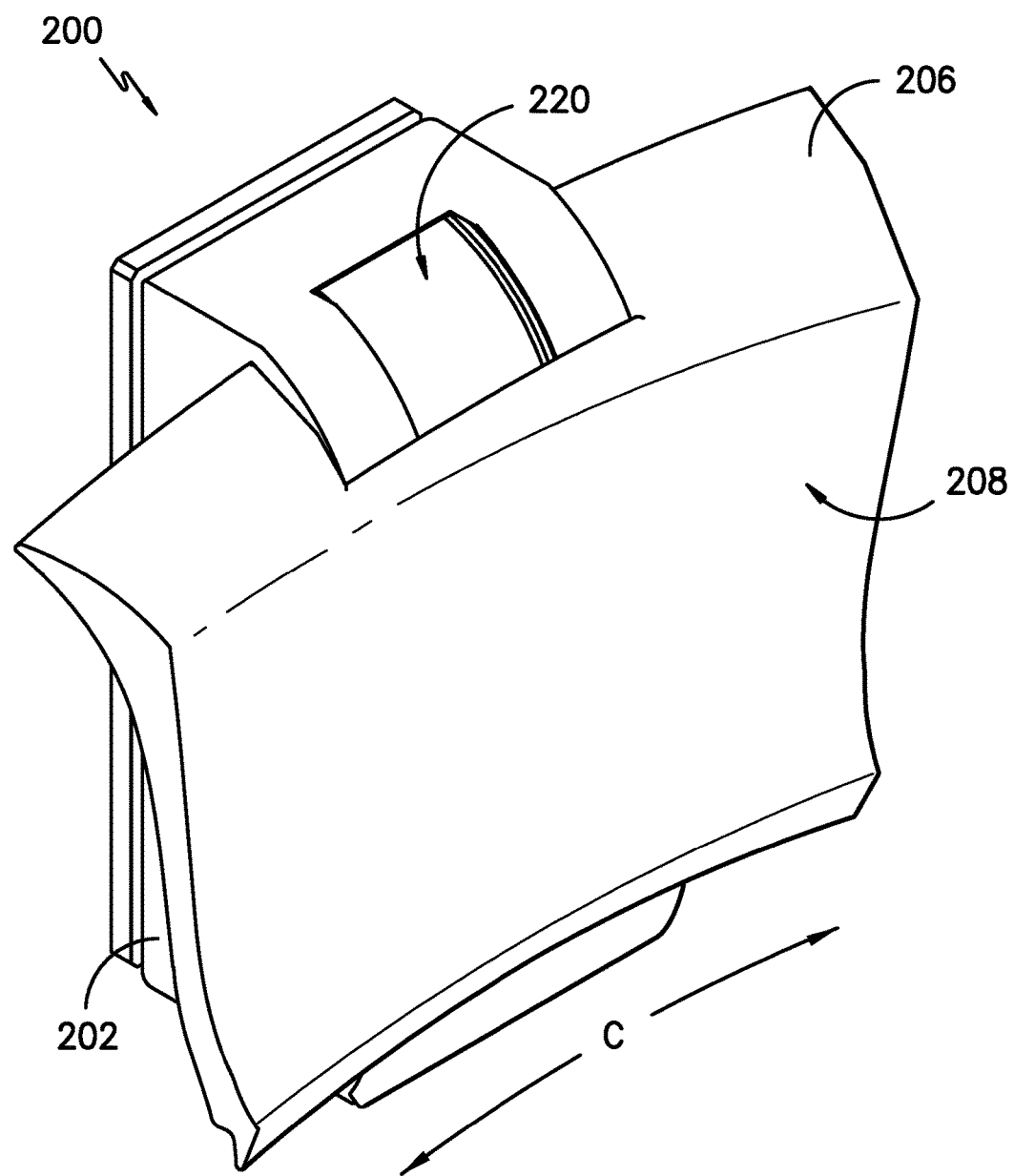
FIG. —10—

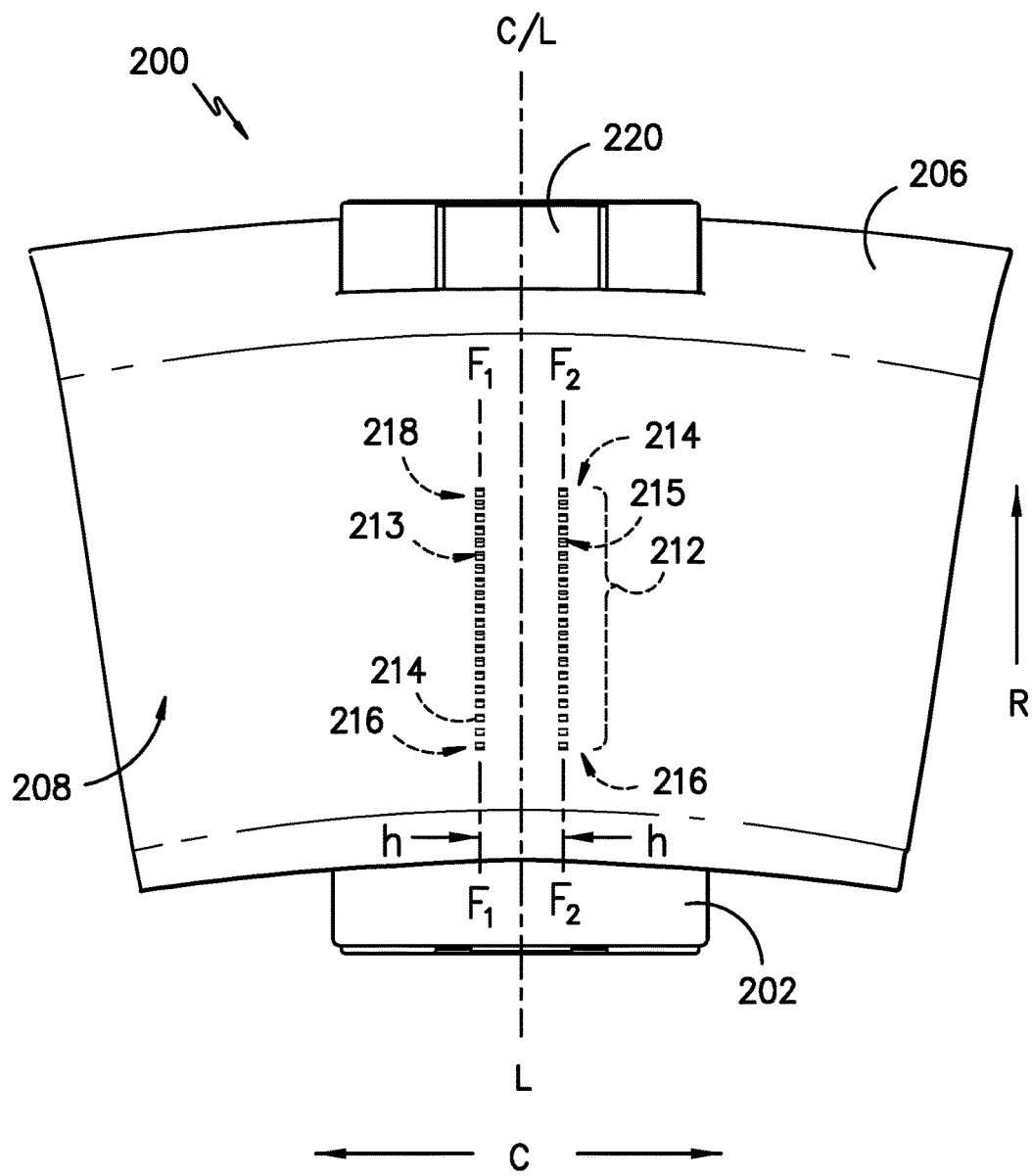
FIG. -11-

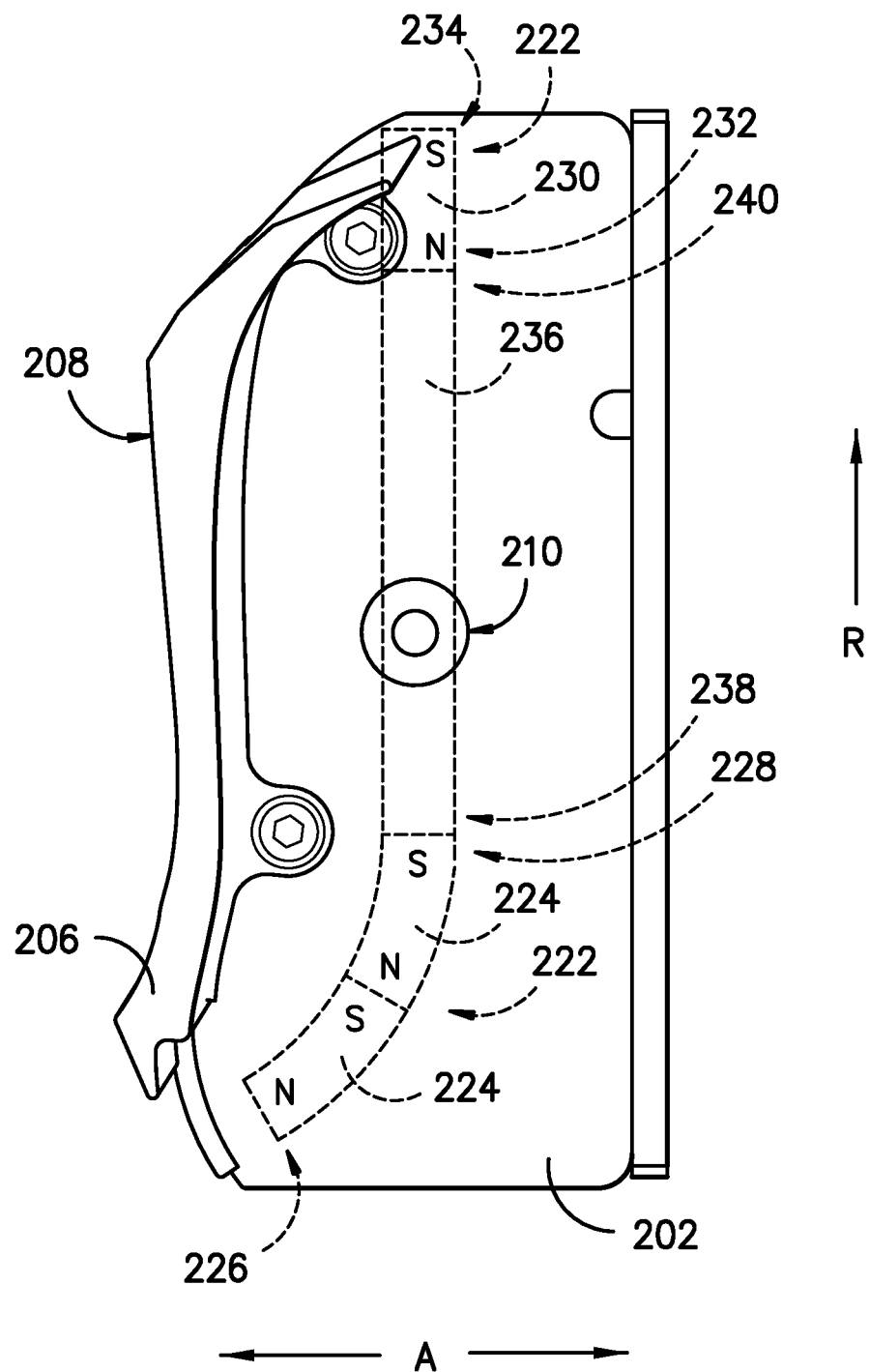
FIG. -12-

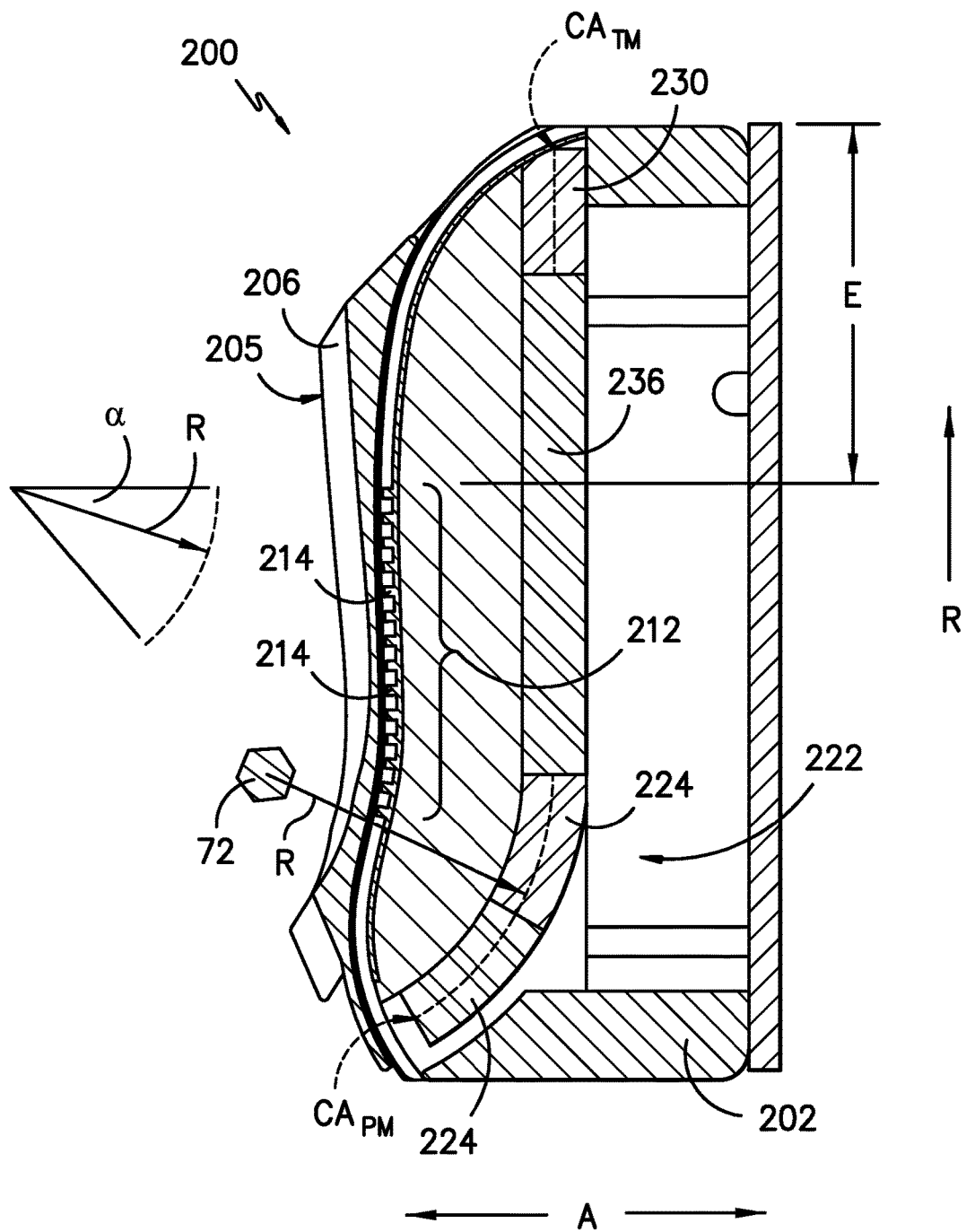
FIG. -13-

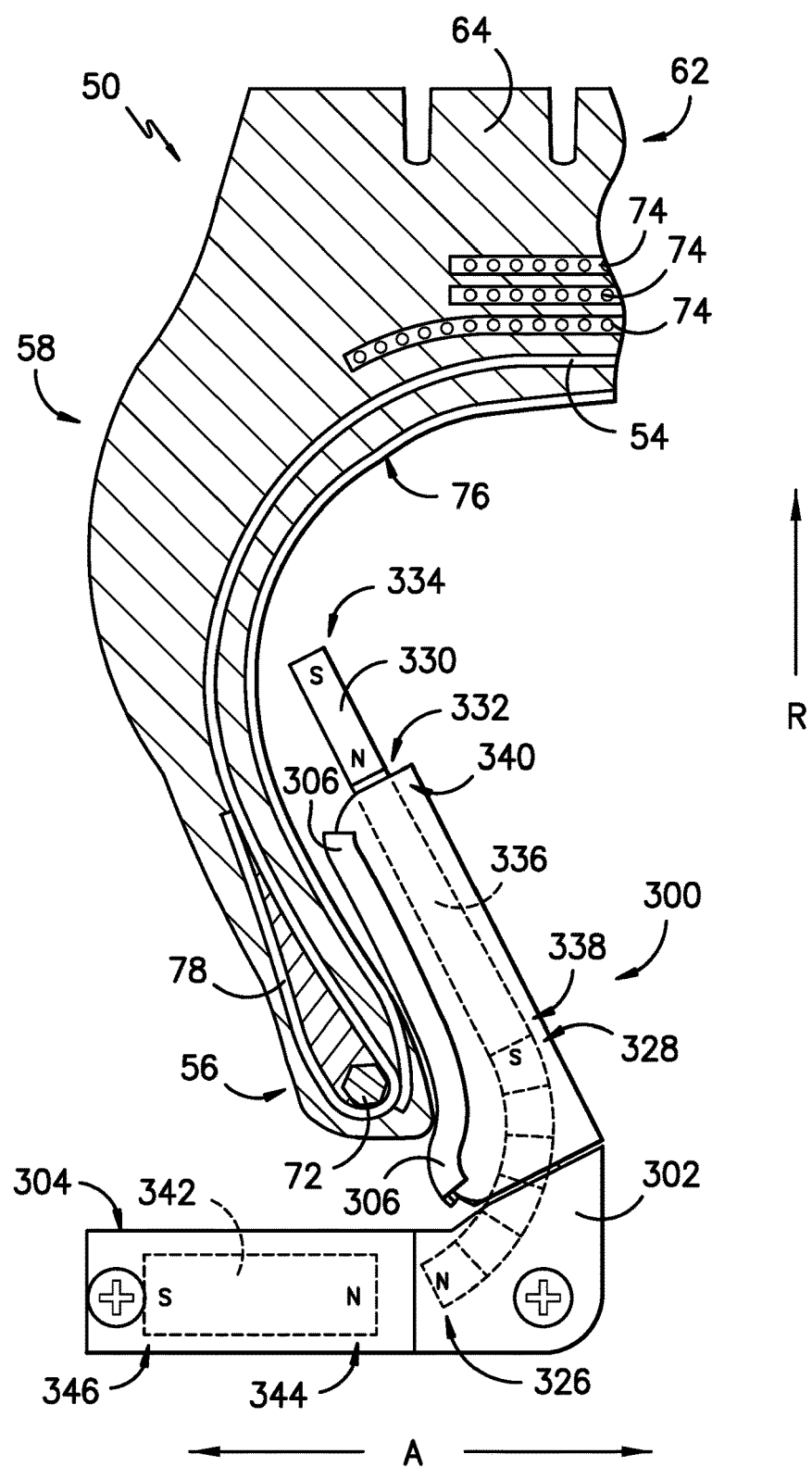
FIG. -14-

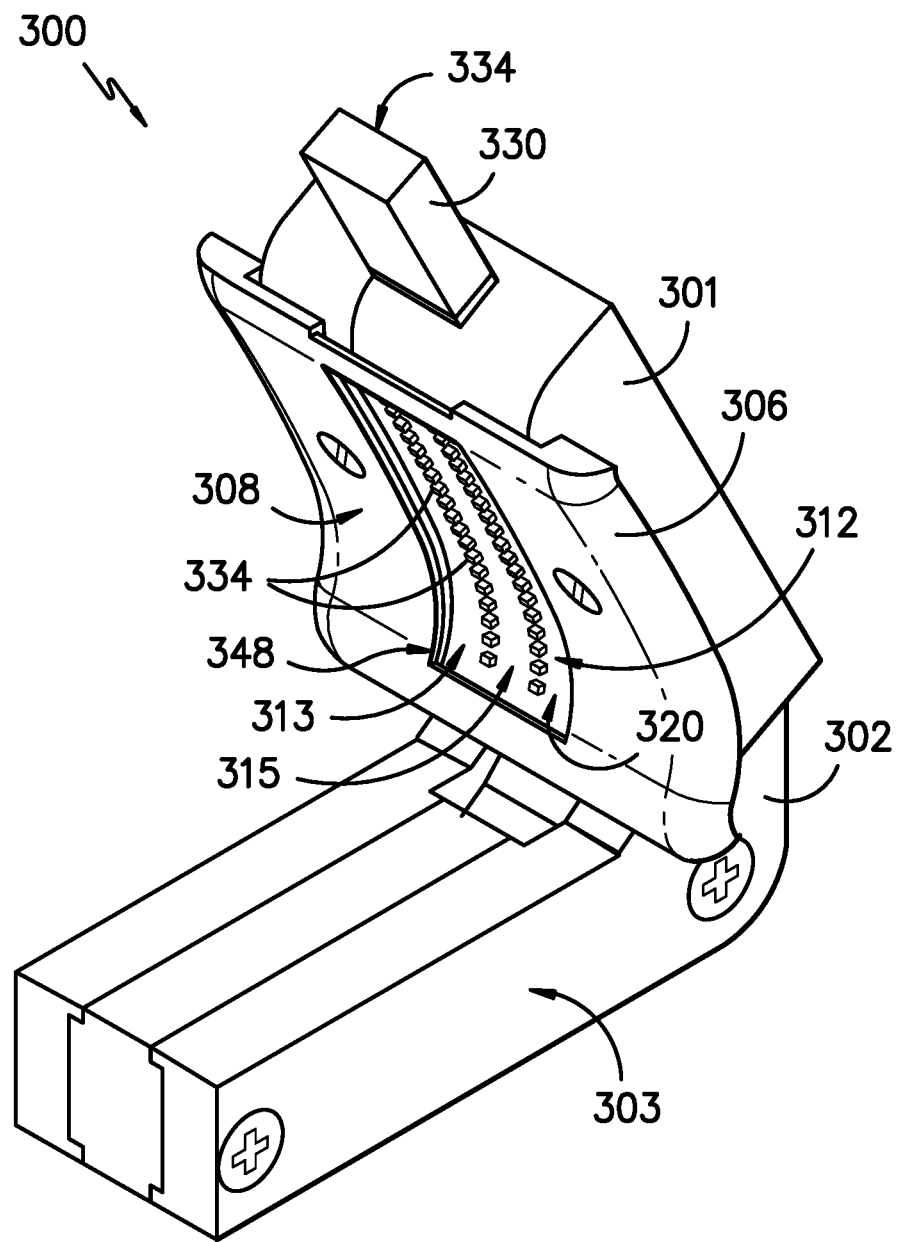
FIG. −15−

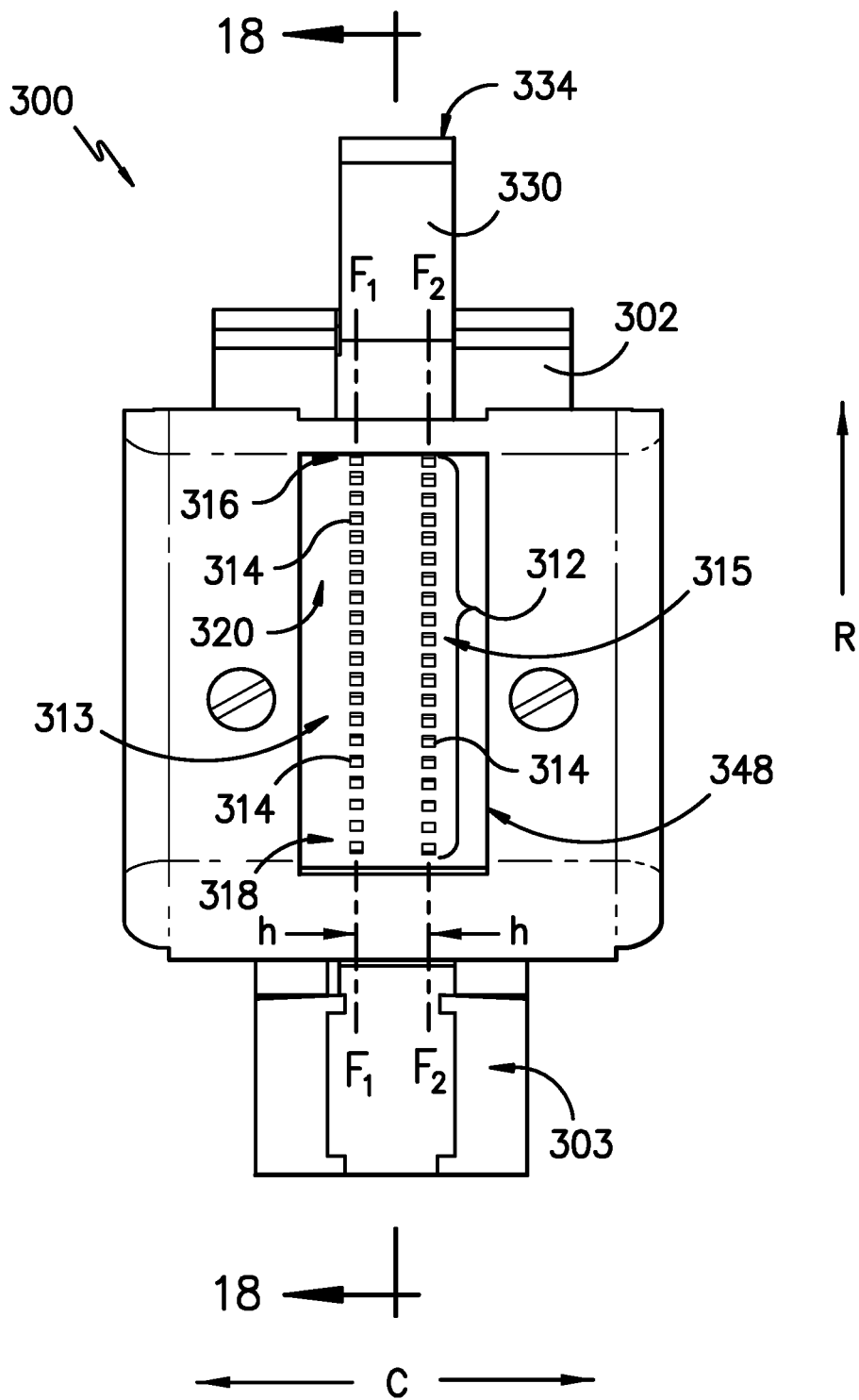
FIG. -16-

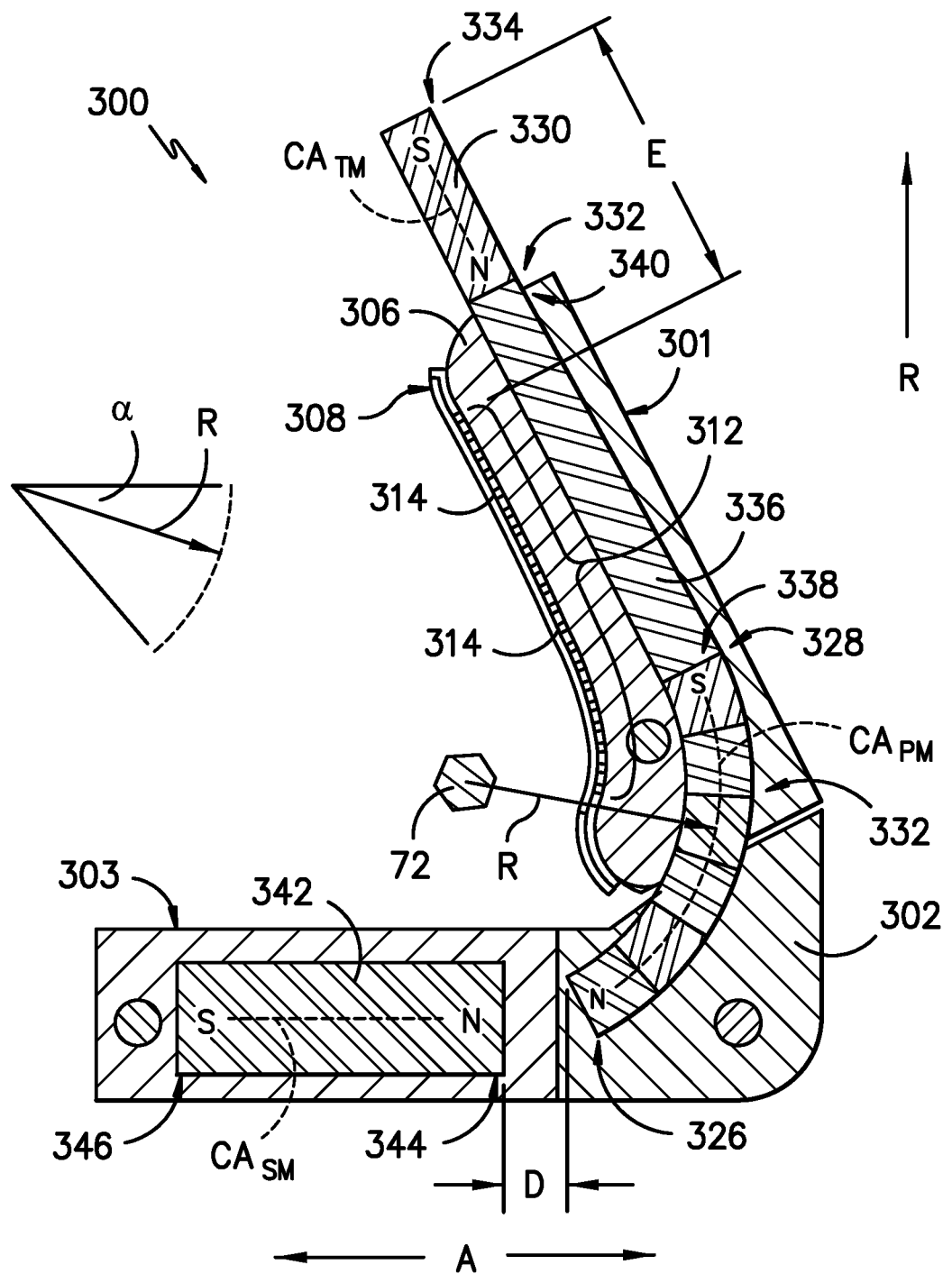
FIG. -17-

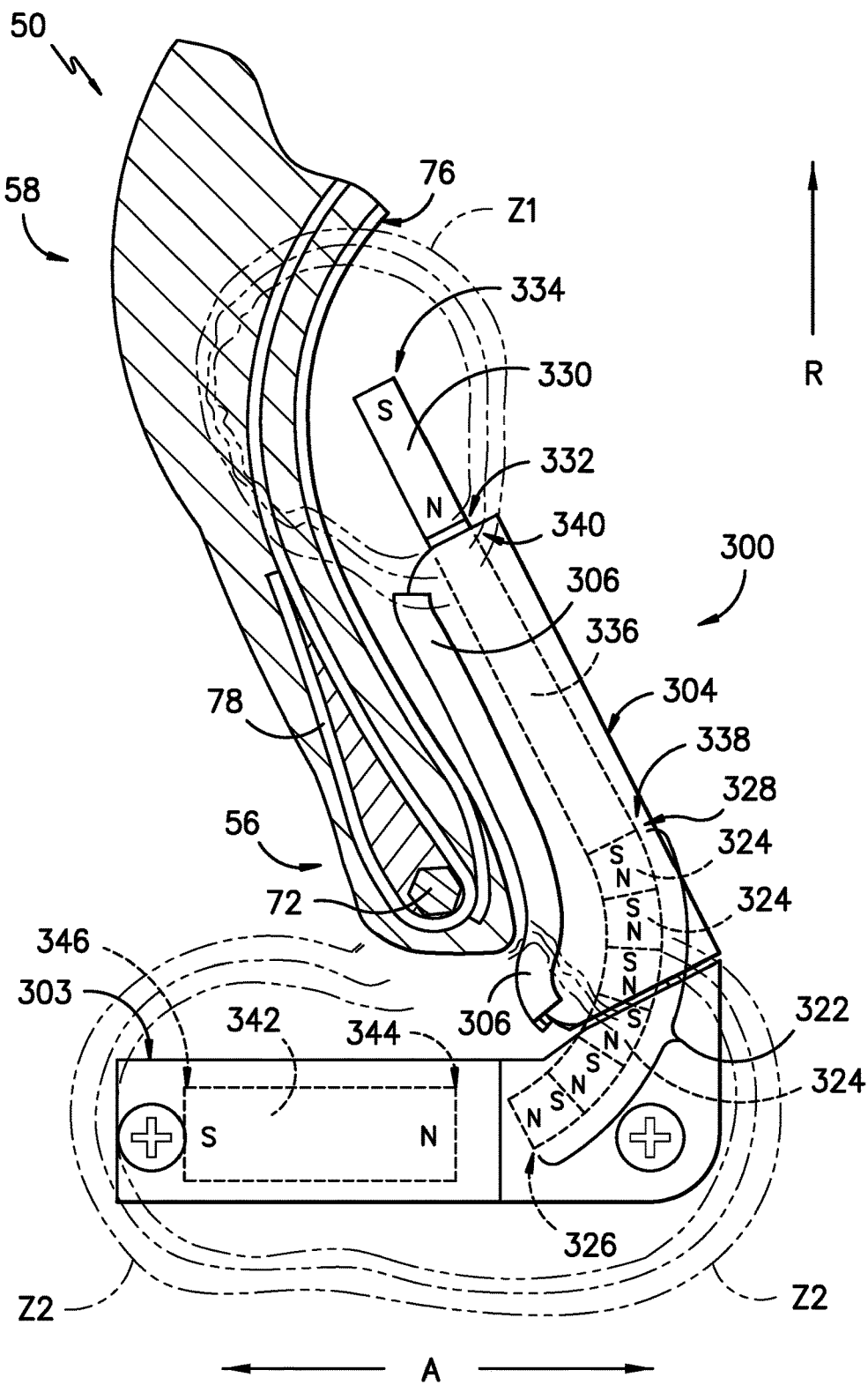
FIG. -18-

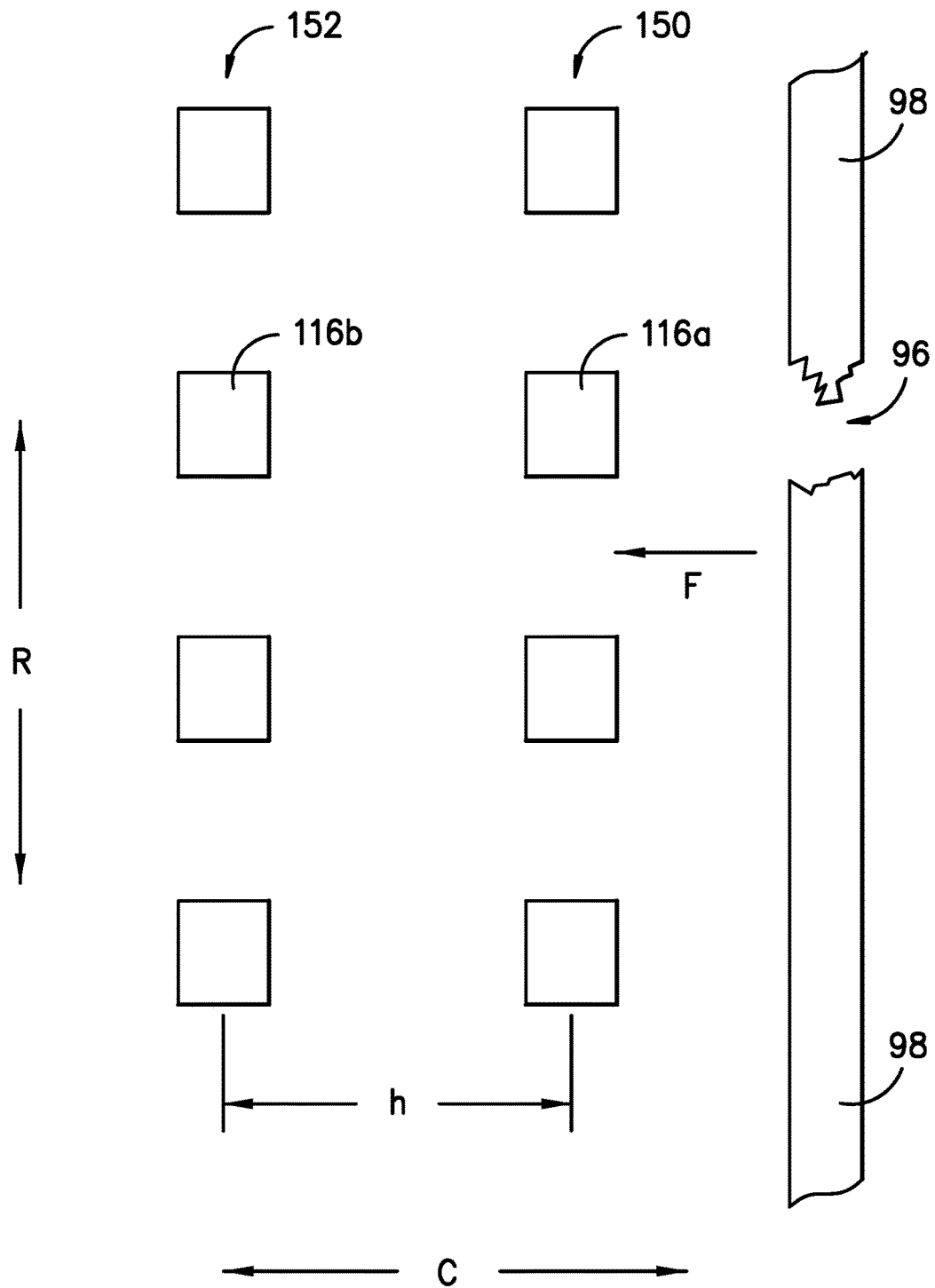
FIG. -19-

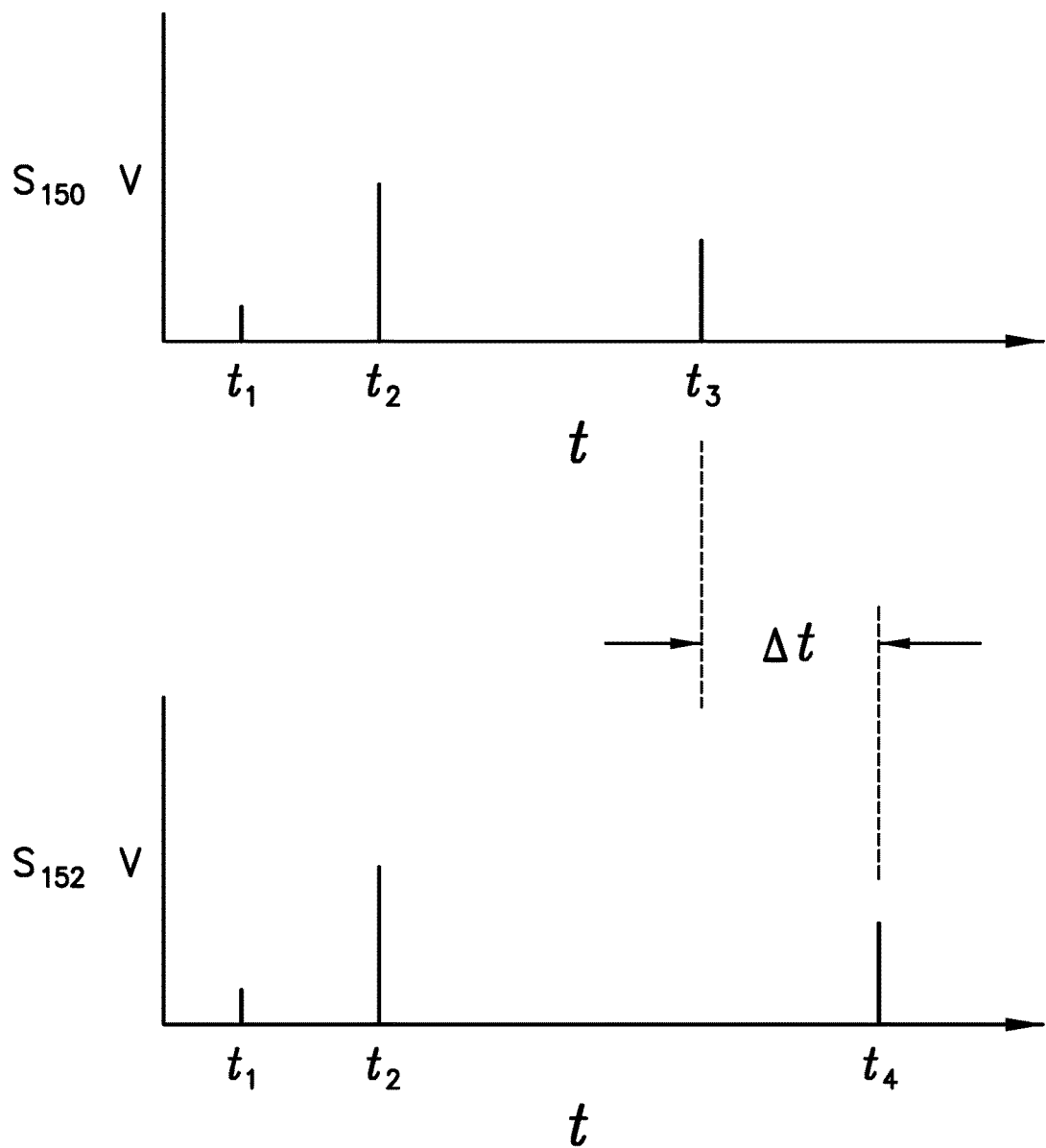
FIG. -20-

METHOD OF USING MULTIPLE ROW SENSING DEVICE FOR A TIRE

PRIORITY CLAIM

The present application is a 371 of International Application Number PCT/US2016/012119 filed Jan. 5, 2016, which is a continuation of and claims priority under 35 U.S.C. § 119 to PCT Application No. PCT/US2015/010159, filed Jan. 5, 2015.

FIELD OF THE INVENTION

The present invention relates generally to a method for detecting damage to reinforcements in a tire.

BACKGROUND OF THE INVENTION

A known tire construction uses a body ply having reinforcement elements that extend from bead portion to bead portion through opposing sidewall portions, and a crown portion of the tire. Sometimes referred to as the carcass ply or reinforcing ply, the body ply is typically anchored at the beads and maintains the overall shape of the tire as the tire is inflated and used. The reinforcement elements of the body ply are usually oriented substantially along the radial direction (a direction perpendicular to the axis of rotation) and can include e.g., a ferrous metal.

During use of the tire, these reinforcement elements (sometimes referred to as cords) may be damaged e.g., from impact with objects in the roadway, travel over curbs, and other damaging events. In some situations, the reinforcement elements may be completely broken as a result of such an event. Unfortunately, this damage may not be readily discoverable from a visual inspection of the exterior of the tire because the reinforcement elements are contained within the rubber materials used to construct the tire.

Commercial tires are commonly reused after a process referred to as retreading. With retreading, worn tread is removed from the tire and a new tread belt or tread section is installed onto the tire. Replacement of the tread is less expensive than replacing the whole tire and allows additional mileage to be obtained using the same tire carcass. This practice is common particularly with commercial tires for heavy trucks.

Before replacing the tread, however, it is advantageous to inspect the tire, including the reinforcement elements of the body ply, for damage or wear. In certain situations, inspection may reveal that replacement of the tire is required rather than retreading. Alternatively, repair of the tire may be required. As stated above, not all damage to interior elements such as e.g., the reinforcement elements of the body ply are readily apparent from a visual inspection alone.

As the reinforcement elements in the body plies for commercial tires such as e.g., heavy truck tires are frequently constructed from a ferrous material, one or more sensors can be used to detect discontinuities in the reinforcement elements such as e.g., breaks that are not otherwise ascertainable from a visual inspection of the tire. It is desirable to automate such an inspection process so that multiple tires may be inspected economically and expediently. However, tires come in a variety of shapes and sizes. More specifically, the profile, height, and width (along the axial direction) can vary substantially from tire to tire. For tire inspection, some sensors require placement at an inner surface of the tire either in contact with the tire or in close proximity thereto. This can be problematic with tire profile and size changes from tire to tire.

Additionally, complexities can be encountered in the detection of discontinuities at certain locations of the tire. For example, the placement of certain sensors in the shoulder portion of the tire along the inner surface can be particularly challenging because the curvature at this portion of the tire and its variability between tires of different sizes and types. More particularly, challenges exist with accurately and consistently positioning one or more sensors at the inner surface of the tire, particularly at the shoulder region, over a range of tire profiles and widths so as to detect e.g., damage to the reinforcement elements of the body ply. In addition, it is preferable that the sensor or sensors are readily removable for use in inspecting another tire.

By way of additional example, detecting damage to the reinforcement elements of the body ply along the bead portion of the tire is also problematic. Each opposing bead portion of the tire typically includes a bead that extends along the circumferential direction forming a hoop or ring. This bead is constructed of ferrous metal that can interfere with accurate detection of damage to the reinforcement elements of the body ply near the bead portion of the tire. More specifically, the bead provides a substantial amount of ferrous metal that impedes the level of saturation of the reinforcement elements with magnetic flux that is desired for break detection. Some tire constructions also use a body ply that is wrapped around the bead, which further increases the amount of ferrous metal in the area where inspection is desired. Additionally, the non-linear geometry of the bead portion also impedes efforts to place the sensors close to the surface of the tire, which is desired for improved detection sensitivity and accuracy. The non-linear geometry and presence of ferrous metal also creates problems in creating fields of magnetic flux that are properly positioned at a level sufficient for damage detection but without undesirably saturating sensors used to detect the magnetic flux.

Vibrations during inspection can also cause problems. More particularly, in order to detect breaks over the entire circumference of the tire, the sensors may be passed over the surface of the tire along the circumferential direction by e.g., rotating the tire relative to the sensor. The interior surface of the tire is rough and unpredictable between different tires and different manufacturers. During movement of the sensor relative to the surface of the tire, the sensor will be bounced or otherwise mechanically agitated. A change in distance between the sensor and the tire will cause a change in the output signal from the sensor. In turn, this can cause false detections and missed detections. Reducing the sensitivity of the sensor to avoid false detections will also reduce the sensor's ability to detect breaks. Algorithms may be used to assist in filtering noise from the signal but such algorithms may be based on assumptions that could also reduce the sensor's ability to detect breaks.

Accordingly, a method of using a device that can be properly positioned along an inner surface of the tire to facilitate inspection of the tire for e.g., breaks or discontinuities in its reinforcements would be useful. Such a method that can also be used to compensate or correct sensor signals that are undesirably based on vibration or mechanical agitation would be particularly useful. Such a method that can be used with a device positionable along the inner surface of various tires at the shoulder regions or bead portions over a range of different tire profiles and widths would also be useful.

SUMMARY OF THE INVENTION

The present invention provides a method of using a sensor device for tire inspection. Signals are received from multiples rows of sensors separated by a predetermined distance. The sensors are positioned next to the inner surface of the tire for inspection. Signals from the different rows of sensors are used to identify e.g., breaks in the reinforcements of the tire and also used to identify undesirable signals generated from vibration or jarring of the sensor device. Additional objects and advantages of the invention will be set forth in part in the following description, or may be apparent from the description, or may be learned through practice of the invention.

In one exemplary method of the present invention, a method of using a sensor device for tire inspection of the reinforcement of a tire is provided. The method includes the steps of positioning a sensor device near the inner surface of the tire, the sensor device having a plurality of sensors arranged along multiple rows; moving the inner surface of the tire past the rows of sensors; generating a first series of signals from a first row of sensors and a second series of signals from a second row of sensors; rejecting signals from the first series and the second series which are not indicative of at least one break in the tire reinforcement; and determining signals from the first series and the second series which are indicative of at least one break in the tire reinforcement.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a cross-sectional view of a portion of an exemplary tire as well as a side view of an exemplary embodiment of the present invention.

FIG. 2 illustrates a perspective view of an exemplary embodiment of the present invention.

FIG. 3 provides a top view of the exemplary embodiment of FIG. 2.

FIG. 4 is a cross-sectional view along lines 4-4 of the exemplary embodiment in FIG. 3.

FIG. 5 is a side view of the exemplary embodiment of FIG. 2.

FIG. 6 is an end view of the exemplary embodiment of FIG. 2.

FIG. 7 is a bottom view of the exemplary embodiment of FIG. 2.

FIG. 8 is a top view of another exemplary embodiment of a sensor device of the present invention.

FIG. 9 illustrates a cross-sectional view of a portion of an exemplary tire as well as a side view of another exemplary embodiment of the present invention.

FIG. 10 illustrates a perspective view of the exemplary embodiment of the present invention shown in FIG. 9.

FIG. 11 illustrates a front view of the exemplary embodiment of the present invention shown in FIG. 9

FIG. 12 is a side view of the exemplary embodiment of FIG. 9.

FIG. 13 is a cross-sectional side view of the exemplary embodiment of FIG. 9.

FIG. 14 is a partial cross-sectional view of one side of a tire along with a side view of another exemplary embodiment of the present invention.

FIG. 15 illustrates a perspective view of the exemplary embodiment of the invention depicted in FIG. 14.

FIG. 16 is a front view of the exemplary embodiment of the invention depicted in FIG. 14.

FIG. 17 is a cross-sectional side view of the exemplary embodiment of FIG. 14.

FIG. 18 is another partial cross-sectional view of one side of a tire and a side view of the exemplary embodiment of FIG. 14 along with a depiction of a magnetic field created by this exemplary embodiment.

FIG. 19 is a schematic view illustrating a sensor detecting a break in the reinforcement of a tire.

FIG. 20 is an exemplary, schematic plot of the series of signals received from two different rows of sensors.

DETAILED DESCRIPTION

For purposes of describing the invention, reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

As used herein, the following definitions apply:

"Meridian plane" is a plane within which lies the axis of rotation of the tire. FIG. 1 is a cross-section of an exemplary tire 50 taken along a meridian plane.

The "crown portion" of the tire is the portion that extends along the axial direction A (which is the direction parallel to the axis of rotation of the tire) between the sidewall portions of the tire including the tread and components positioned radially inward of the tread.

"Body ply" or "carcass" or "carcass ply" is a ply that extends between and from the bead portions on opposing sides of the tire, through the opposing sidewall portions, and across the crown portion of the tire. The body ply may include ferrous reinforcements.

The "radial direction" is perpendicular to the axis of rotation of the tire and is denoted in the figures with an "R" and a directional arrow. The axial direction, parallel to the axis of rotation, is denoted in the figures with an "A" and directional arrows.

The "circumferential direction" of the tire (also referred to as the longitudinal direction) is the direction corresponding to the periphery of the tire and is defined by the direction of rotation of the tire during normal operation. The circumferential direction is denoted in the figures with a C and directional arrows.

In the description that follows, directions R, A, and C are denoted in drawings of the exemplary embodiments to denote the orientation of the embodiments relative to the tire when the sensor device is positioned for tire inspection. Additionally, the positions of various components of exemplary embodiments may be described with reference to these directions as determined relative to sensor device 100 when it is positioned for tire inspection.

FIG. 1 illustrates a cross-sectional view of an exemplary tire 50 along a meridian plane. A side view of an exemplary embodiment of a sensor device 100 of the present invention is removably positioned at an inner surface 52 of tire 50 for purposes of tire inspection. The construction of tire 50 includes a body ply 54 that extends from bead portions 56 and 58, through opposing sidewall portions 58 and 60, and through crown portion 62 with tread 64. Sensor device 100 is shown along a shoulder portion 66 of tire 100. Sensor device 100 is not limited to use along shoulder portion 66. Instead, sensor device 100 can be readily placed at other locations along the inner surface 52 of tire 50. Certain embodiments of the sensor device of the present invention, as described herein, are particularly suited for use along the shoulder portion of a variety of tire sizes of different widths and profiles.

For this exemplary embodiment, sensor device 100 is removably positioned within the interior 68 of tire 50 along inner surface 52 by a positioning system that includes a support arm 70. Sensor device 100 is pivotally connected to support arm 70 at point P, which allows the orientation of device 100 to be adjusted to more readily match the profile of the inner surface 52 of tire 50. Support arm 70 can be connected at point of attachment 130 (FIG. 2) and is provided by way of example only. Other positioning systems may be used with sensor device 100 as well.

Sensor device 100 is useful for inspecting tire 50 particularly where it is desirable to position one or more sensors in close proximity to the inner surface 52 of tire 50. Body ply 54 includes reinforcement elements typically constructed from a ferrous material and embedded in the rubber materials used to construct tire 50. As previously stated, reinforcement elements can be damaged during use of tire 50. During a tire inspection process, as may be part of e.g., a retreading operation, tire 50 may be inspected for damage to such reinforcement elements. For example, sensor device 100 may include one or more Hall Effect sensors as will be further described herein for detecting breaks in ferrous reinforcement elements.

While inspection of the reinforcement elements will be used by way of example, using the teachings disclosed herein, one of ordinary skill in the art will understand that sensor device 100 can be useful for other tire inspections using other sensor types where placement of the sensor(s) in close proximity to the inner surface of the tire is desired—and particularly where placement of one or more sensors along the shoulder region of tires of various sizes and profiles is desired. For example, sensor device 100 may include Hall Effect sensors, temperature sensors, optical sensors, and/or other type sensors as well.

During inspection, sensor device 100 may be placed very close (e.g., within 5 mm to 6 mm) of inner surface 52 or may contact surface 52 as shown in FIG. 1. Once positioned, tire 50 can be rotated about its axis of rotation so as to scan or detect for broken reinforcement elements over a complete circumference of the tire. Sensor device 100 allows the placement of one or more sensors in close proximity to inner surface 52, which may be necessary for proper testing and also expedites testing by allowing a complete inspection from a single rotation of tire 50.

As shown in FIG. 2, sensor device 100 includes a body 102 that may be constructed from e.g., an inner portion 104 and an outer portion 106. Body 102 includes an outermost inspection surface 108. As used herein, "outermost" means that the inspection surface 108 is the closest part of body 102 to that portion of the inner surface 52 of tire 50 that is being inspected.

Referring now to all figures, body 102 defines a longitudinal direction L and width direction W that is orthogonal to direction L. When body 102 is placed along the inner surface 52 of tire 50, body 102 is oriented such that the longitudinal direction L is orthogonal to the circumferential direction C of tire 50 (FIGS. 2 and 5). Body 102 includes an aperture 110 defined by outermost inspection surface 108. Aperture 110 extends longitudinally along direction L between a first end 112 and a second end 114 of outermost inspection surface 108 (FIG. 3).

As best shown in FIGS. 2, 3, and 6, a plurality of sensors 116 are arranged side-by-side or adjacent to one another along longitudinal direction L. Sensors 116 are positioned within aperture 110 such that sensors 116 are surrounded by outermost inspection surface 108. Sensors 116 are supported upon a sensor support surface 118 (which may e.g., a printed circuit board or other substrate) that may be slightly recessed or positioned inwardly relative to outermost inspection surface 108. As shown, sensor support surface 118 is parallel to the outermost inspection surface 108. More particularly, sensor support surface 118 has a curvature or profile along the longitudinal direction L that matches the profile of outermost inspection surface 108.

Sensors 116 are arranged along multiple rows that are adjacent to each other along the width of body 102 and along circumferential direction C. Specifically, for this exemplary embodiment, sensor device 100 includes sensors 116 arranged linearly along a first row 150 and along a second row 152. First row 150 defines a first axis $F_1$ and second row 152 defines a second axis $F_2$ as shown in FIG. 3. While only two rows 150 and 152 are shown, more than two rows of sensors 116 may be used in other exemplary embodiment of the invention as well. As will be further described, the use of multiple rows of sensors 116 allows compensation for vibrations or jarring of device 100 that may occur during inspection.

For the exemplary embodiment as depicted in FIG. 3, first axis $F_1$ and second axis $F_2$ are adjacent and parallel to each other and separated by a distance d. However, in other embodiments, sensors 116 may be arranged linearly along axes that are not parallel to each other. Turning to another exemplary embodiment shown in FIG. 8, for example, first axis $F_1$ and second axis $F_2$ are positioned at a non-zero angle α with respect to each other. Angle α may be, for example, in the range of 0 degrees<α≤4 degrees. In still another embodiment, angle α may be about 1 degrees. Other angles may be used as well. The use of a non-zero angle α between first axis $F_1$ and second axis $F_2$ may allow sensors 116 to more closely match the radial angle of reinforcements within the tire. FIG. 8 also indicates that sensors 116 may be mounted onto two separate sensor support surfaces 118a and 118b as well.

In certain embodiments of the invention, sensors 116 are Hall Effect sensors 116, which detect magnetic flux and can provide a signal indicative of the presence of magnetic flux as well as the magnetic flux density and, therefore, can be used to detect changes in magnetic flux density. In one embodiment of the invention, thirty-two Hall Effect sensors are used and are positioned at intervals I of about 2.5 mm (see, e.g., FIG. 3) along their respective axis. For detecting breaks in the reinforcements of body ply 54, the use of multiple Hall Effect sensors 116 improves the effectiveness of the sensor device 100 in detecting breaks. More particularly, shoulder portion 66 of tire 50 is a high flexion zone for the tire and, therefore, a location where breaks in the reinforcements of body ply 54 are likely to be found. The use of multiple sensors ensures at least one sensor 116 will be located on each side of a break in shoulder portion 66 as tire 50 is rotated during the inspection process.

Referring now to FIGS. 1, 4, and 5, the outermost inspection surface 108 has a particular profile when viewed along the longitudinal-direction L as shown in these figures. More particularly, when sensor device 100 is placed against the inner surface of tire 50 (as in FIG. 1), the outermost inspection surface 108 has a profile of an arc of a circle. The arc of this circle has a radius R (FIG. 5) that is orthogonal to the circumferential direction C of tire 50 when sensor device 100 is positioned against inner surface 52 as shown in FIG. 1. The profile of outermost inspection surface 108 along its width (W) is substantially flat (FIG. 6). A similar construction is used for the exemplary embodiment of FIG. 8.

For the exemplary embodiments of FIGS. 1 through 8, the inventors have discovered that the profile for the outermost inspection surface 108 matches the shape of the inner surface of most tires along the shoulder zone when radius R (FIG. 5) is in the range of 50 mm to 75 mm. This allows sensor device 100 to be used over a wide variety of tire shapes and sizes. More particularly, the profile allows the placement of sensors 116 in close proximity to inner surface 52 so that tire 50 can be properly inspected by a single rotation of tire 50 past sensor device 100.

In one exemplary embodiment, the inventors have determined that when radius R is about 74 mm, the profile of the outermost inspection surface 108 will match the shape of the inner surface of approximately 85 percent of the heavy truck/commercial truck tire profiles that are commercially available. In another exemplary embodiment, the inventors have determined that when radius R is about 52 mm, the profile of the outermost inspection surface 108 will match the shape of the inner surface of the other approximately 14 percent of the heavy truck/commercial truck tire profiles that are commercially available.

As shown in FIG. 4, when sensors 116 are Hall Effect sensors, device 100 can be equipped with a permanent magnet 122 in order to create fields of magnetic flux used in detecting breaks in ferrous reinforcements. As shown, body 102 defines a compartment 124 into which magnet 122 is received. For this exemplary embodiment, magnet 122 is oriented with a longitudinal axis LA that is parallel to a line T that is tangent to outermost detection surface 108 at the centerline C/L of device 100. This orientation ensures a specific field of magnetic flux is created relative to the plurality of sensors 116. More than one magnet may be used as well.

As also shown in FIG. 4, sensor device 100 can be equipped with a protective cap 120 to protect sensors 116. Cap 120 is received into aperture 110 and covers sensors 116. As such, cap 120 can protect sensors 116 from damage during the inspection process where tire 50 is rotated past sensor device 100.

FIG. 9 illustrates a side view of an exemplary embodiment of sensor device 200 of the present invention in position for inspection of a representative tire 50. Only a portion of a cross-section along a meridian plane of tire 50 is shown as tire 50 is substantially symmetrical about its centerline as viewed in the meridian plane. Tire 50 includes bead portion 56 with bead 72. A body ply 54 extends from bead portion 56, through sidewall portion 58, and through crown portion 62 along both sides of tire 50. Crown portion 62 includes a tread portion 64 and belt plies 74 located radially inward of tread portion 64.

For this exemplary embodiment, sensor device 200 is removably positioned at bead portion 56 of tire 50 and adjacent to portion of its inner surface 76. Sensor device 200 may be repeatably located along the bead portion 56 of multiple tires as may be required e.g., in a commercial facility by a positioning system (not shown) that can be connected at point of attachment 210. Sensor device 200 is useful for inspecting tire 50 particularly where it is desirable to position one or more sensors in close proximity to the inner surface 76 of tire 50 at bead portion 56 along with one or more magnets that create a field of magnetic flux for use in damage detection.

More particularly, as previously indicated, body ply 54 includes reinforcement elements (not shown) typically constructed from a ferrous material and embedded in the rubber materials used to construct tire 50. Reinforcement elements can be damaged during use of tire 50. During a tire inspection process, as may be part of e.g., a retreading operation, tire 50 may be inspected for damage to such reinforcement elements. For example, sensor device 200 may include one or more Hall Effect sensors for detecting breaks in ferrous reinforcement elements. In other exemplary embodiments of the invention, sensor device 200 may include Hall Effect sensors, temperature sensors, optical sensors, and/or other type sensors as well.

When sensor device 200 is positioned for inspection of tire 50, sensor device 200 may be placed very close (e.g., within 5 mm to 6 mm) of inner surface 76 at bead portion 56 or may even contact inner surface 76. Once positioned, tire 50 can be rotated about its axis of rotation so as to scan or detect for broken reinforcement elements over a complete circumference of the tire. Sensor device 200 allows the placement of one or more sensors in close proximity to inner surface 76 near bead portion 56, which may be necessary for proper testing and also expedites testing by allowing a complete inspection from a single rotation of tire 50.

In addition, because of the unique positioning of an array of magnets relative to the sensors, the present invention will create a field of magnetic flux that can be used to detect damage to the ferrous reinforcement elements near bead portion 56 despite the presence of a substantial amount of ferrous components at bead portion 56 including bead 72, body ply 54, and the turn-up 78 of body ply 54 that may be wrapped around bead 72 as shown in FIG. 9. At the same time, the sensors will not be oversaturated with magnetic flux, which could impede the accuracy of tire inspection.

Referring now to FIGS. 9, 10, 11, 12, and 13, sensor device 200 includes a body 202 that may be constructed from one or more parts formed integrally or attached. Body 202 includes a platform 206 that defines an outermost inspection surface 208 (FIG. 10). As used herein, "outermost" means that the inspection surface 208 is the closest part of body 202 to that portion of the inner surface 76 of tire 50 that is being inspected by the sensors. Outermost inspection surface 208 has a profile as viewed along one side (FIGS. 9 and 12) that is slightly concave in order to facilitate its positioning adjacent to inner surface 76. Outermost inspection surface 208 is also slightly curved along the circumferential direction C (FIG. 10)

As shown in FIG. 11, sensor device 200 includes a sensor array 212 located proximate to outermost inspection surface 208. For this exemplary embodiment, sensor array 212 includes multiple adjacent rows 213, 215 of sensors 214 positioned on sensor support surface 220 located immediately beneath or behind outermost inspection surface 208. Sensors 214 in first row 213 are arranged linearly adjacent to each other along first axis F1 while sensors 214 in second row 215 are arranged linearly adjacent to each other along second axis F2. As with previous embodiments, first axis F1 and F2 may be parallel to each other or positioned at a non-zero angle α. Each row 213 and 215 also includes a first opposing end 216 separated from a second opposing end 218 along longitudinal direction L. For this exemplary embodiments rows 213 and 215 are equally spaced about a centerline of sensor device 200 as shown in FIG. 11.

For this exemplary embodiment, sensors 214 are configured as Hall Effect sensors to detect magnetic flux and provide a signal indicative of the presence of magnetic flux including changes in magnetic flux density. While any number of Hall Effect sensors may be used depending upon the detection length desired for sensor array 212, in one exemplary embodiment of the invention a total of 16 Hall Effect sensors are in each row 213 and 215 for a total of 32 Hall Effect sensors. Other configurations may be used as well.

Referring now to FIGS. 9, 12, and 13, sensor device 200 also includes at least one magnet array 222. For this exemplary embodiment, magnet array 222 is arranged on body 202 so that the outer inspection surface 208 and sensor array 212 are closer to inner surface 76 than magnet array 222. In some embodiments, magnet array 222 is arranged on body 202 so that outer inspection surface 208 and sensor array 212 are between at least a portion of the magnet array 222 and tire 50 when sensor device 200 is positioned for tire inspection as shown in FIG. 9. In other embodiments of the invention, more than one magnet array may be used. By way of example, the magnet arrays may be arranged adjacent to each other along circumferential direction C.

Magnet array 222 includes a plurality of magnets 224 having a first end 226 and a second end 228. (FIG. 12). The plurality of magnets 224 are arranged sequentially with alternating polarity as shown in FIG. 13. As used herein, "arranged sequentially with alternating polarity" means adjacent magnets 224 are oriented with opposite poles facing each other such as e.g., N-S/N-S/N-S or S-N/S-N/S-N.

At least a portion of the plurality of magnets 224 are arranged into an arc of a circle. For this exemplary embodiment, the plurality of magnets 224 contact each along the arc and define a central axis $CA_{PM}$ (FIG. 14). Central axis $CA_{PM}$ lies in the same plane (a meridian plane of tire 50) as the longitudinal direction L and centerline C/L positioned between rows 213 and 215 of sensor array 112 in this embodiment.

The arc of the circle has a radius R and a central angle α. When sensor device 200 is positioned for tire inspection, radius R originates in bead 72 and sweeps over central angle α, which is in the range of 60 degrees to 90 degrees, or 60 degrees≤α≤90 degrees. This arrangement of at least a portion of the plurality of magnets 224 into the arc of a circle ensures that such magnets 224 at least partially surround bead portion 72. For the exemplary embodiment shown in FIGS. 10 through 14, central angle α is about 60 degrees.

Continuing with FIGS. 12 and 13, magnet array 222 also includes a terminal magnet 230 having a first end 232, a second end 234, and also defining a central axis $CA_{TM}$. As shown, first end 232 is located radially inward of second end 234. Second end 234 is displaced along longitudinal direction L by a predetermined distance E from the second end 218 of sensor array 212. More particularly, predetermined distance E represents the distance between second end 234 of terminal magnet 230 and the second opposing end 218 of sensor array 212. This displacement of second end 234 ensures that the plurality of sensors 214 of sensor array 212 are not overly saturated with magnetic flux, which could interfere with proper detection of damage to that portion of the reinforcements in body ply 54 located adjacent to outermost inspection surface 208 during tire inspection. In one exemplary embodiment, predetermined distance E is about 10 mm to about 15 mm. In another exemplary embodiment, predetermined distance E is about 13 mm. The polarity of terminal magnet 230 is also arranged sequentially with alternating polarity relative to the plurality of magnets 224.

Sensor device 200 includes a connecting bar 236 having a first end 238 and a second end 240. Connecting bar 236 may be constructed from ferrous metal such as steel and is used to help distribute magnetic flux created by the plurality of magnets 224 and the terminal magnet 130. Connecting bar 236 extends between second end 228 of the plurality of magnets 224 and first end 232 of terminal magnet 230.

In one exemplary embodiment, connecting bar 236 has a cross-sectional area (in a plane perpendicular to the meridian plane of tire 50) at first end 238 that is substantially equal to the cross-sectional area of the second end 228 of plurality of magnets 224. Similarly, connecting bar 236 has a cross-sectional area at second end 238 that is substantially equal to the cross-sectional area of the first end 232 of terminal magnet 230.

In an alternative embodiment of the present invention, connecting bar 236 may be replaced by extending the plurality of magnets 224. More particularly, for this alternative embodiment, the plurality of magnets 224 can be extended linearly along longitudinal direction L and into contact with (or proximate to) first end 232 of terminal magnet 230. The extension of the plurality of magnets 224 could be accomplished with multiple magnets arranged sequentially with alternating polarity or by a single magnet having a length comparable to connecting bar 234. Regardless, such magnets or magnet would be arranged sequentially with alternating polarity between the magnets 224 in the arc of the circle and terminal magnet 230. In addition, although shown as a single magnet, terminal magnet 230 could be a plurality of magnets arranged sequentially with alternating polarity provided that second end 234 is displaced by predetermined distance E as already described.

FIGS. 14 through 18 illustrate another exemplary embodiment of a sensor device 300 of the present invention, wherein the use of the same or similar reference numerals denotes the same or similar features as already described for the exemplary embodiment of FIGS. 9 through 13. In the exemplary embodiment of FIGS. 14 through 18, sensor device 300 includes a sensor body 302 having a first arm portion 301 and a second arm portion 303 (FIGS. 15 and 17) that form an acute angle with respect to one another. First arm portion 301 supports sensor array 312 and magnet array 322. In addition, for this exemplary embodiment, magnet array 322 includes a supplemental magnet 342 supported by second arm portion 303.

Supplemental magnet 342 has a central axis $CA_{SM}$ (FIG. 17) extending along axial direction A. For this exemplary embodiment, central axis $CA_{SM}$ lines within the same plane as central axis $CA_{PM}$ and central axis $CA_{TM}$. This plane would also be coplanar with a meridian plane of tire 50 when sensor device 300 is properly positioned for tire inspection. It should be understood that in other exemplary embodiments, the three central axes $CA_{SM}$, $CA_{PM}$ and central axis $CA_{TM}$ may not line in the same plane.

As shown, supplemental magnet 342 has a first end 344 separated longitudinally along $CA_{SM}$ by a second end 346. First end 344 of supplemental magnet 342 and first end of plurality of magnets 124 are positioned radially inward of bead portion 52 when sensor device 300 is in position for tire inspection (as shown in FIGS. 14 and 18). In addition, the first end 344 of supplemental magnet 342 has a polarity that is the same as the polarity of the first end 326 of plurality of magnets 324. For this exemplary embodiment, first end 326 and first end 344 are separated by a predetermined distance D (FIG. 17). In one embodiment, predetermined distance D is in the range of 5 mm to 15 mm. In another embodiment, predetermined distance D is about 10 mm. Although shown as a single magnet, supplemental magnet 342 could be a plurality of magnets arranged sequentially with alternating polarity provided that first end 344 is displaced by predetermined distance D as already described.

The exemplary embodiment of FIGS. 14 through 18 includes an aperture 348 in outermost inspection surface 308 that surrounds sensor array 312. Sensor support surface 320 is slightly recessed relative to outmost inspection surface 308 so as to protect sensor array 312 during tire inspection. Other configurations may be used as well.

Referring to FIGS. 15 and 16, sensor device 300 includes a sensor array 312 located proximate to outermost inspection surface 308. For this exemplary embodiment, sensor array 312 includes multiple adjacent rows 313, 315 of sensors 314 positioned on sensor support surface 320 located immediately beneath or behind outermost inspection surface 308. Sensors 314 in first row 313 are arranged linearly adjacent to each other along first axis F1 while sensors 314 in second row 315 are arranged linearly adjacent to each other along second axis F2. As with previous embodiments, first axis F1 and F2 may be parallel to each other or positioned at a non-zero angle α. Each row 313 and 315 also includes a first opposing end 316 separated from a second opposing end 318 along longitudinal direction L. For this exemplary embodiments rows 213 and 215 are equally spaced about a centerline of sensor device 300.

FIG. 18 provides an example of the use of sensor device 300 for inspection of tire 50. More particularly, FIG. 18 shows representative fields Z1 and Z2 of magnetic flux created by magnet array 322. As shown, field Z1 is created along a shoulder region of sidewall 58 while field Z2 is created around bead portion 56. Importantly, the magnetic flux does not overly saturate sensor array 312, which would preclude accurate detection of breaks in the reinforcements of body ply 54 in the region of interest. At the same time, enough magnetic flux is provided for detection despite the presence of substantial ferrous material in bead portion 72.

For each of the embodiments of a sensor device 100, 200, and 300 set forth above, sensors 116 are arranged linearly along at least adjacent two rows that are offset by a predetermined distance h (see FIGS. 3, 8, 11, and 16). The rows are arranged such that once the sensor device 100, 200, or 300 is positioned against a tire, the movement of the device over the inner surface 52 of the tire will cause the portion of the tire measured to pass each row of sensors sequentially.

The exemplary embodiment 100 of FIGS. 1 through 6 will now be used to describe exemplary methods of operation of the invention. As will be understood by one or ordinary skill in the art using the teachings disclosed herein, similar methods of operation apply to sensor devices 200 and 300 and other methods may be used as well.

Rotating tire 50 past sensor device 100 positioned as shown in FIG. 1 at shoulder portion 66 will cause a break in the metal reinforcements of body ply 54 in shoulder portion 66 to pass each row of sensors 150 and 152. FIG. 19, for example, depicts a ferrous reinforcement 98 of body ply 54 having a break 96. It is desirable to detect the presence and location of break 96 during an inspection of tire 50. Accordingly, as previously depicted in FIG. 1 for example, sensor device 100 is positioned near inner surface 52 of tire 50. As depicted by arrow F, sensor device 100 is caused to pass over inner surface 52. The direction of movement F is along the same direction that distance h extends between sensor rows 150 and 152. Such movement may be accomplished by e.g., rotating tire 50 along its circumferential direction C past a stationary sensor device 100 or by moving stationary sensor device 100 past tire 50. Depending upon irregularities and other aspects of inner surface 52, such movement may jar or vibrate sensor device 100.

During such movement, each row of sensors 150 and 152 generates a series of signals $S_{150}$ and $S_{152}$ over time as schematically depicted in FIG. 20. For example, row 150 generates signals at times $t_1$, $t_2$ and $t_3$ while row 152 generates signals a times $t_1$, $t_2$, and $t_4$. These signals $S_{150}$ and $S_{152}$ could be e.g., voltage outputs V from sensors 116 in rows 150 and 152, respectively. Other types of outputs could be provided as well. The representation of the signal outputs in FIG. 20 is provided by way of example only.

Because the longitudinal direction L of sensor device 100 is parallel to the radial direction R of the tire, break 96 will pass each row 150 and 152 at different times rather than simultaneously. For example, break 96 will first be detected by sensor 116a in row 150 and then by sensor 116b in row 152. Other adjacent sensors 116 in each row may also help detect break 96. The magnitude of the time interval required for the break to pass each row 150 and then 152, referred to herein as predetermined time period Δt, will depend on e.g., the relative speed of movement of the tire past sensors 116, the distance h between rows 150 and 152, sampling rate used for sensors 116, and/or other factors. For example, the magnitude of predetermined time period Δt may be proportional to the magnitude of distance h. Regardless, predetermined tire period Δt can be readily determined by experiment or modeling, and then used as described herein to compensate for signals cause by e.g., vibration of sensor device 100 that are not indicative of a break.

By way of example, in FIG. 20, during tire inspection sensor row 150 generates a series of signal $S_{150}$ that includes signals at times $t_1$ and $t_2$. During the same tire inspection, sensor row 152 generates a series of signal $S_{152}$ that also includes signals at times $t_1$ and $t_2$. In other words, sensor row 150 and 152 simultaneously generated signals at times $t_1$ and $t_2$. Because these signals occur at the same times—i.e. $t_1$ and $t_2$—these signals can be rejected or disregarded as not indicative of at least one break in the tire reinforcements of body ply 54. Instead, the signals at $t_1$ and $t_2$ were created by vibration or jarring of sensor device 100. Additionally, the magnitude of the signals at $t_1$ and $t_2$ from sensor rows 150 and 152 is the same or similar, which further confirms that these signals should be rejected as not indicative of at least one break in the tire reinforcements of body ply 54.

However, sensor row 150 also created a signal at time $t_3$ and sensor row 152 created a signal at time $t_4$. Time $t_4$ occurs after time $t_3$ and, more importantly, occurs after $t_3$ by the amount of the predetermined time period Δt. As such, the signals at times $t_3$ and $t_4$ can be determined as indicative of at least one break in the reinforcement of body ply 54. Additionally, the magnitude of the signals at $t_3$ and $t_4$ from sensor rows 150 and 152 is the same or similar, which further confirms that these signals should be accepted as indicative of at least one break in the tire reinforcements of body ply 54.

Other methods of analyzing the signals to determine which signals are indicative of a break versus which signals should be rejected as indicative of e.g., vibration may be used as well. One exemplary method of analyzing the signals from both rows of sensors includes opening a window or a time offset to detect for similar shapes and slopes between the two series of signals. For example, assume a sampling rate of 800 hertz is used for sensors 116 in each row at a speed of rotation of tire 50 that results in a range of approximately 25 to 36 sample counts per degree of rotation. At these sampling rates, the offset in time would be approximately 30 to 50 milliseconds per degree of offset between the two rows of sensors (where degree of offset refers to the distance extending along a direction of movement of the inner surface relative to the sensors during the step of moving. This would translate to 180 to 300 milliseconds if the two rows of sensors were 6 degrees apart, and so on. Again, this offset in time is dependent on the relational speed between tire and sensors and sampling rate.

Another exemplary method of analyzing the series signals from different rows of sensors such as 150 and 152 compares the signals and then uses an "and" type function analysis. If the leading row (row 150 in the example of FIG. 19) indicates a rapid change in the signals "and" the subsequent row (row 152 in the example of FIG. 19) also indicates similar changes, this is due to a mechanical agitation of sensor device. If the leading row indicates a rapid change "and" the subsequent row does not see the same changes, then this would be indicative of an anomaly or break in the reinforcements.

In still another exemplary method of analyzing the two signals, a differential analysis is performed between two sensors at the same radial position in the tire. When a mechanical agitation occurs, the differential between the two signals would not change. When the leading sensor changes as it approaches an anomaly or break, a differential would occur between the two signals.

All of the previously described exemplary methods may be performed in real time. Alternatively, the signals (e.g., $S_{150}$ and $S_{152}$) could be stored and analyzed at some time after the inspection.

Another method of analyzing the offset signals could be to offset the second row signals after the collection of data from the inspection. The total number of sample counts would then be known, and then the second row of signals could be shifted in time a calculated amount knowing the sample rate and sensor separation. The signals could then be compared to each other for similar changes such as similar voltage changes.

Other methods could be used to create a constant number of sample counts per tire which could lead to a constant number of sample points between the two rows of sensors. As an example, the tire could be turned by the bead instead of the exterior tread, and using position feedback from the bead rollers, either the speed of rotation or sampling rate could be adjusted to achieve a constant number of samples for each test. Still other methods may be used as well.

As used herein, the term "method" or "process" refers to one or more steps that may be performed in other ordering than shown without departing from the scope of the presently disclosed invention. As used herein, the term "method" or "process" may include one or more steps performed at least by one electronic or computer-based apparatus. Any sequence of steps is exemplary and is not intended to limit methods described herein to any particular sequence, nor is it intended to preclude adding steps, omitting steps, repeating steps or performing steps simultaneously. As used herein, the term "method" or "process" may include one or more steps performed at least by one electronic or computer-based apparatus having a processor for executing instructions that carry out on or more steps.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A method for tire inspection, the tire having reinforcements and an inner surface, the method comprising the steps of:
   positioning a sensor device near the inner surface of the tire, the sensor device having a plurality of sensors arranged along multiple rows;
   moving the inner surface of the tire past the rows of sensors;
   generating a first series of signals from a first row of sensors and a second series of signals from a second row of sensors;
   rejecting signals from the first series and the second series which are not indicative of at least one break in the tire reinforcement; and
   determining signals from the first series and the second series which are indicative of at least one break in the tire reinforcement.

2. The method for tire inspection as in claim 1, wherein the step of rejecting comprises:
   identifying signals in the first series and the second series that occur simultaneously; and
   disregarding these signals as not indicating at least one break in the tire reinforcements.

3. The method for tire inspection as in claim 1, wherein the step of rejecting comprises:
   identifying signals in the first series and the second series that occur simultaneously and that have a similar magnitude; and
   rejecting these signals as not indicating at least one break in the tire reinforcements.

4. The method for tire inspection as in claim 1, wherein the step of determining comprises:
   identifying at least one signal in the second series that occurs after at least one signal in the first series by a predetermined time interval, $\Delta t$.

5. The method for tire inspection as in claim 1, wherein the step of determining comprises:
   identifying at least one signal in the second series that occurs after at least one signal in the first series by a predetermined time interval, $\Delta t$, and that has a similar signal magnitude as the at least one signal in the first series.

6. The method for tire inspection as in claim 5, wherein the predetermined time interval, $\Delta t$, is determined at least in part by a distance, h, between the first row of sensors and the second row of sensors, the distance extending along a direction of movement of the inner surface relative to the sensors during the step of moving.

7. The method for tire inspection as in claim 6, wherein the predetermined time interval, $\Delta t$, is determined at least in part by a relative speed of movement of the inner surface relative to the sensors during the step of moving.

8. The method for tire inspection as in claim 7, wherein the predetermined time interval, $\Delta t$, is determined at least in part by a sampling rate that is used for the first row of sensors and the second row of sensors.

9. The method for tire inspection as in claim 8, wherein the tire defines a circumferential direction, and wherein the step of moving comprises rotating the tire along the circumferential direction past the sensors.

10. The method for tire inspection as in claim 1, wherein the tire defines a circumferential direction, and wherein the step of moving comprises rotating the tire along the circumferential direction past the sensors.

11. The method for tire inspection as in claim 1, wherein the sensors are arranged linearly along the first row and the second row.

12. The method for tire inspection as in claim 11, wherein the first row of sensors and the second row of sensors are parallel to each other.

13. The method for tire inspection as in claim 11, wherein the first row of sensors and the second row of sensors are positioned at a non-zero angle of five degrees or less from each other.

14. The method for tire inspection as in claim 11, wherein the sensors comprise Hall Effect sensors.

15. The method for tire inspection as in claim 11, further comprising the step of storing the first series of signal and the second series of signals before the steps of rejecting and determining.

* * * * *